United States Patent
NG Pitti et al.

(10) Patent No.: US 11,325,119 B2
(45) Date of Patent: May 10, 2022

(54) UNIVERSAL APPROACH FOR DECOUPLING SENSITIVITY AND DYNAMIC RANGE OF A SENSOR

(71) Applicant: President and Fellows of Harvard College, Cambridge, MA (US)

(72) Inventors: Carlos Francisco NG Pitti, Jamaica Plain, MA (US); Ulri Nicole Lee, Seattle, WA (US); Richard Novak, Boston, MA (US); Olivier Yves Frederic Henry, Brookline, MA (US); Remco Van Erp, Sint Anthonis (NL); Donald E. Ingber, Boston, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 229 days.

(21) Appl. No.: 16/494,230

(22) PCT Filed: Mar. 14, 2018

(86) PCT No.: PCT/US2018/022478
§ 371 (c)(1),
(2) Date: Sep. 13, 2019

(87) PCT Pub. No.: WO2018/170156
PCT Pub. Date: Sep. 20, 2018

(65) Prior Publication Data
US 2021/0322976 A1     Oct. 21, 2021

Related U.S. Application Data

(60) Provisional application No. 62/472,180, filed on Mar. 16, 2017, provisional application No. 62/471,932, filed on Mar. 15, 2017.

(51) Int. Cl.
*B01L 3/00*     (2006.01)
*G01N 27/08*     (2006.01)
*G01N 33/487*     (2006.01)

(52) U.S. Cl.
CPC ... *B01L 3/502707* (2013.01); *B01L 3/502715* (2013.01); *G01N 27/08* (2013.01);
(Continued)

(58) Field of Classification Search
CPC ......... B01L 3/502707; B01L 3/502715; B01L 2300/0645; B01L 2300/0896;
(Continued)

(56) References Cited

U.S. PATENT DOCUMENTS 7,569,340 B2    8/2009    Mirkin
8,431,390 B2    4/2013    Jovanovich
(Continued)

FOREIGN PATENT DOCUMENTS

WO    WO 2012/016136 A2    2/2012
WO    WO 2015/138034 A2    9/2015
(Continued)

OTHER PUBLICATIONS

How to embed three-dimensional flexible electrodes in microfluidic devices for cell culture applications. / Pavesi, Andrea; Piraino, Francesco; Fiore, Gianfranco B.; Farino, Kevin M.; Moretti, Matteo; Rasponi, Marco. Lab on a Chip—Miniaturisation for Chemistry and Biology, vol. 11, No. 9, 07.05. (Year: 2011).*
(Continued)

*Primary Examiner* — Jennifer Wecker
*Assistant Examiner* — Jonathan Bortoli
(74) *Attorney, Agent, or Firm* — Nixon Peabody LLP

(57) ABSTRACT

A fluidic device includes a fluidic layer, a capture material, and an electronics layer, the fluidic layer includes a main channel and a pair of sample channels fluidly coupled to the main channel. The pair of sample channels is configured to receive and introduce a sample material into the device. The sample material includes an analyte. The capture material is positioned in a portion of the main channel that is spaced
(Continued)

from the pair of sample channels. The capture material has a three-dimensional matrix of receptors therein configured to bond with the analyte. The capture material has a length that is associated with a dynamic range of the fluidic device and a cross-sectional area that is associated with a sensitivity of the fluidic device. The electronics layer includes electrodes configured to measure an electrical resistance through a portion of the capture material.

36 Claims, 16 Drawing Sheets

(52) U.S. Cl.
CPC .. *G01N 33/48707* (2013.01); *B01L 2300/069* (2013.01); *B01L 2300/0645* (2013.01); *B01L 2300/0867* (2013.01); *B01L 2300/0896* (2013.01)

(58) Field of Classification Search
CPC ....... B01L 2300/069; B01L 2300/0867; G01N 27/08; G01N 33/48707
See application file for complete search history.

(56) References Cited

U.S. PATENT DOCUMENTS

| | | |
|---|---|---|
| 2012/0028811 A1 | 2/2012 | Craighead |
| 2013/0040313 A1 | 2/2013 | Afzali-Ardakani |
| 2015/0119280 A1 | 4/2015 | Srinivas |
| 2016/0061822 A1 | 3/2016 | Sa'ar |
| 2017/0010259 A1* | 1/2017 | Amoabediny ..... G01N 33/5438 |

FOREIGN PATENT DOCUMENTS

| | | | |
|---|---|---|---|
| WO | WO-2015138034 A2 * | 9/2015 | ............ C12M 23/16 |
| WO | WO 2015/179712 A1 | 11/2015 | |

OTHER PUBLICATIONS

He, M. et al., "Microfluidic Polyacrylamide Gel Electrophoresis with in Situ Immunoblotting for Native Protein Analysis"; Anal. Chem. vol. 81, No. 19, pp. 8177-8184; Sep. 4, 2009 (8 pages).

Burns, M. et al. "An Integrated Nanoliter DNA Analysis Device"; Science, vol. 282, No. 5388, pp. 484-487; Oct. 26, 1998 (4 pages).

Shafiee, H. et al.; "A Microfluidic System for Biological Particle Enrichment Using Contactless Dielectrophoresis"; Journal of the Association for Laboratory Automation (JALA), vol. 25, No. 3, pp. 224-232; Jun. 2010 (9 pages).

International Search Report and Written Opinion of International Searching Authority for PCT/US2018/022478, dated Jun. 25, 2018 (20 pages).

Martinez-Duarte, R., "Microfabrication Technologies in Dielectrophoresis Applications—a review"; Electrophoresis, vol. 33, No. 21, Nov. 1, 2012 (52 pages).

Kim, J. et al., "Hybridization of DNA to Bead-Immobilized Probes Confined within a Microfluidic Channel"; Langmuir, vol. 22, No. 24, pp. 10130-10134; Nov. 21, 2006 (5 pages).

* cited by examiner

Microfluidics 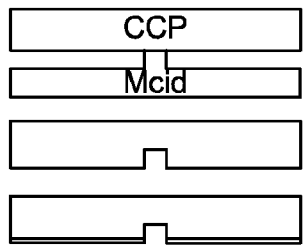
Electrodes 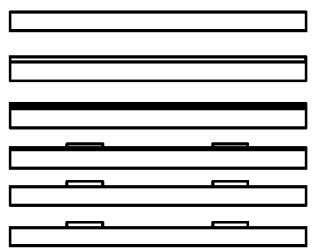
Bonding 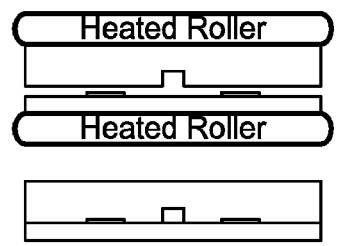
FIG. 15A
FIG. 15B
FIG. 15C
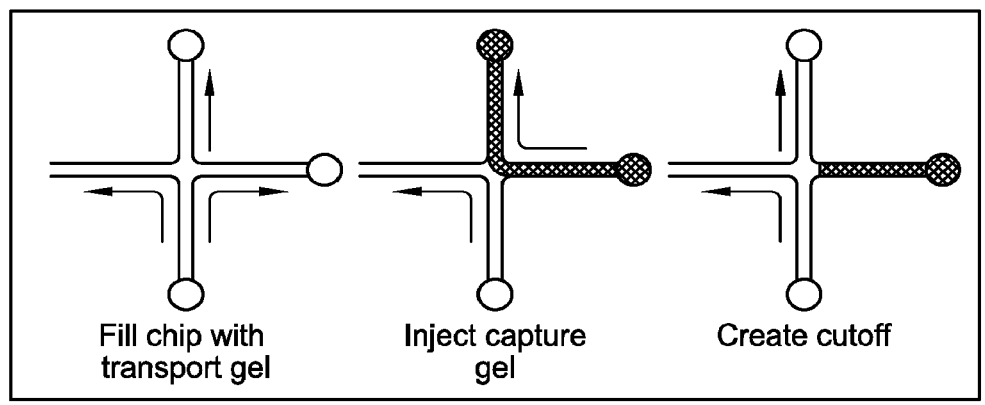
FIG. 16A
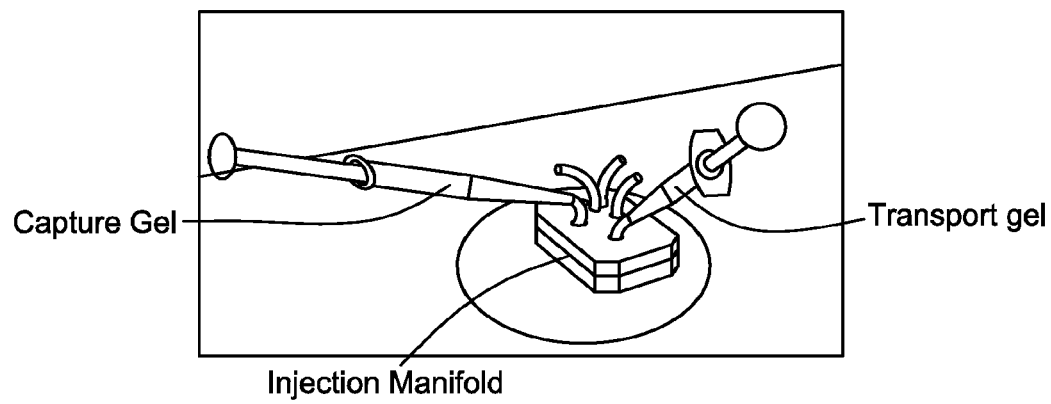
FIG. 16B

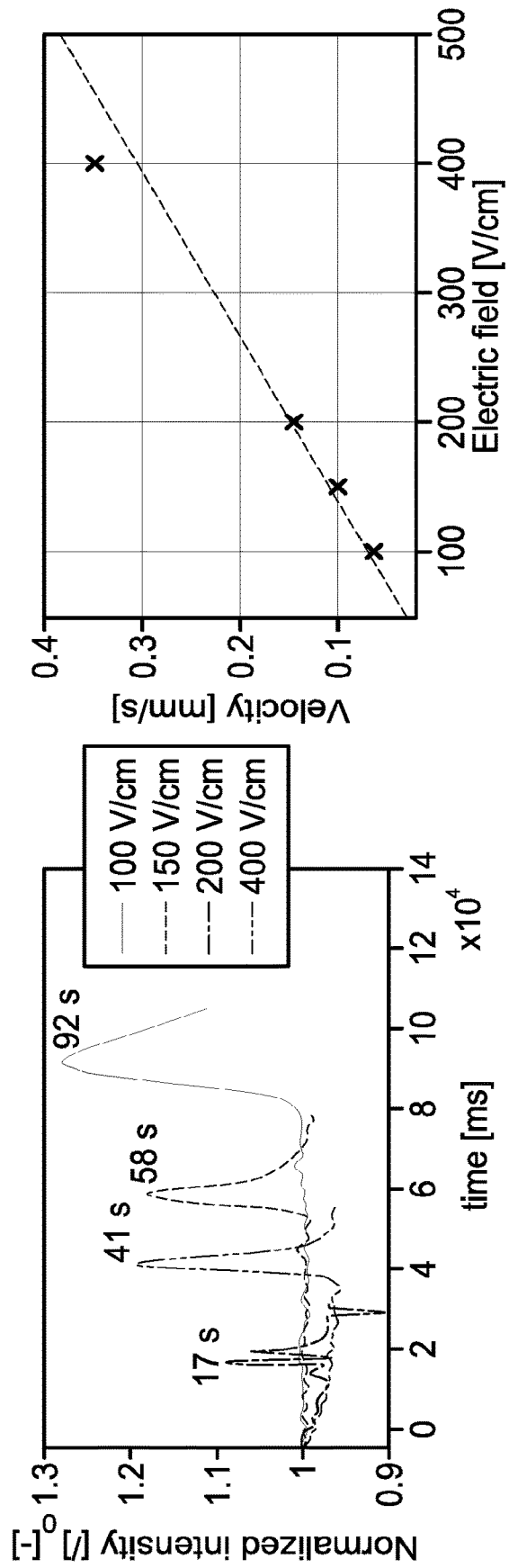
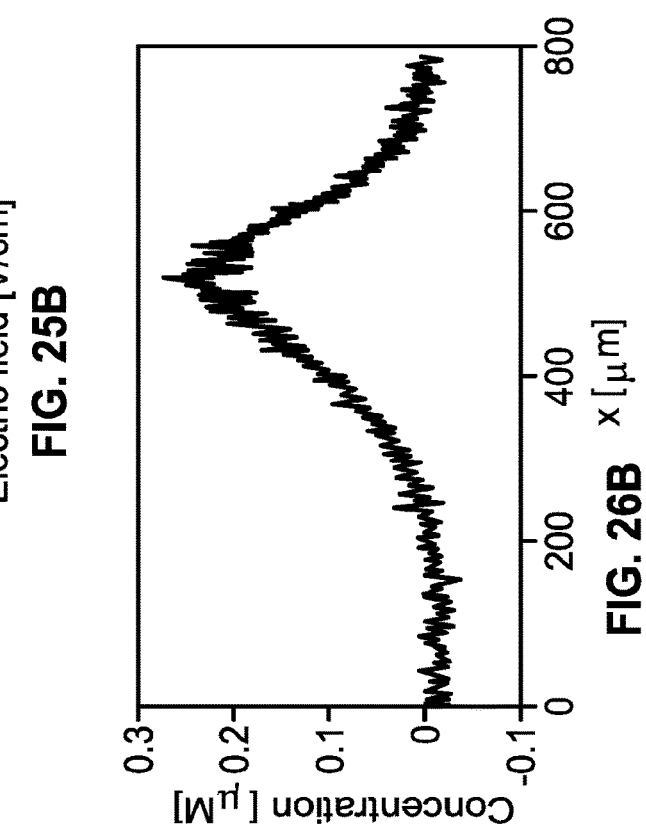
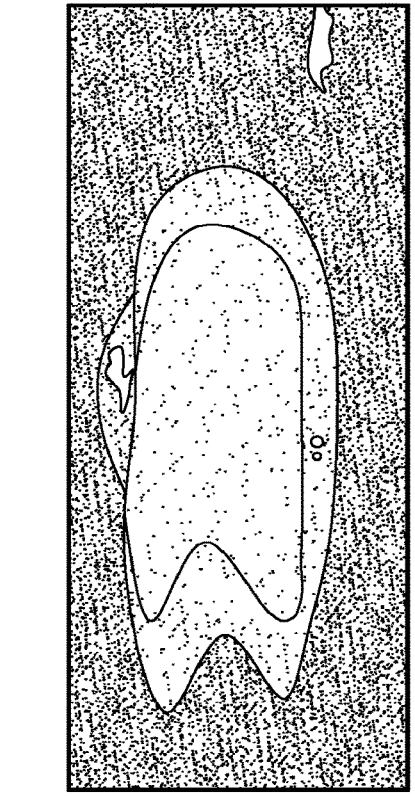
FIG. 25A
FIG. 25B
FIG. 26A
FIG. 26B

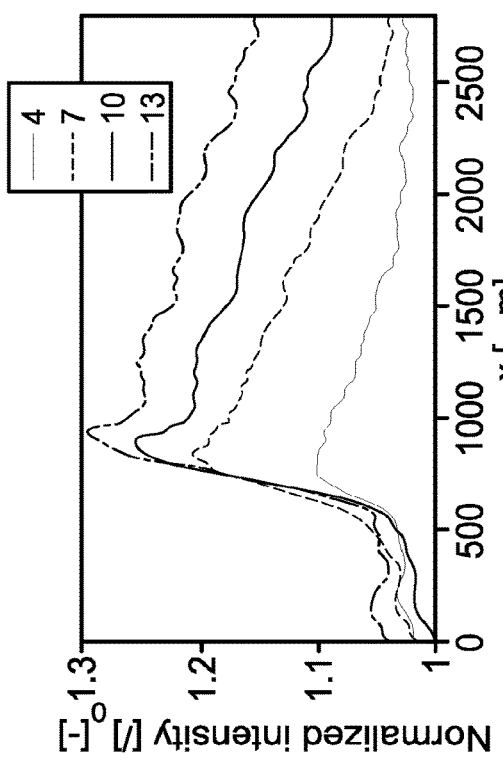
FIG. 27B
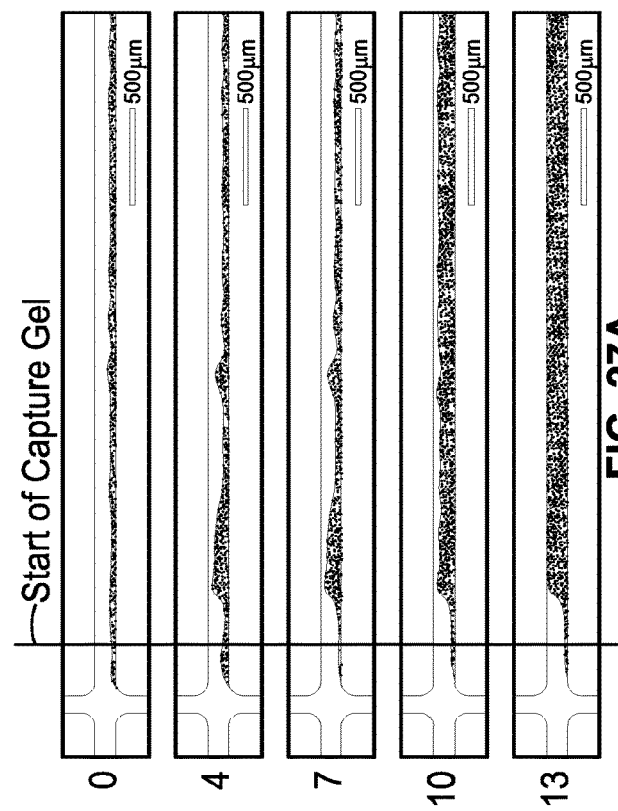
FIG. 27A
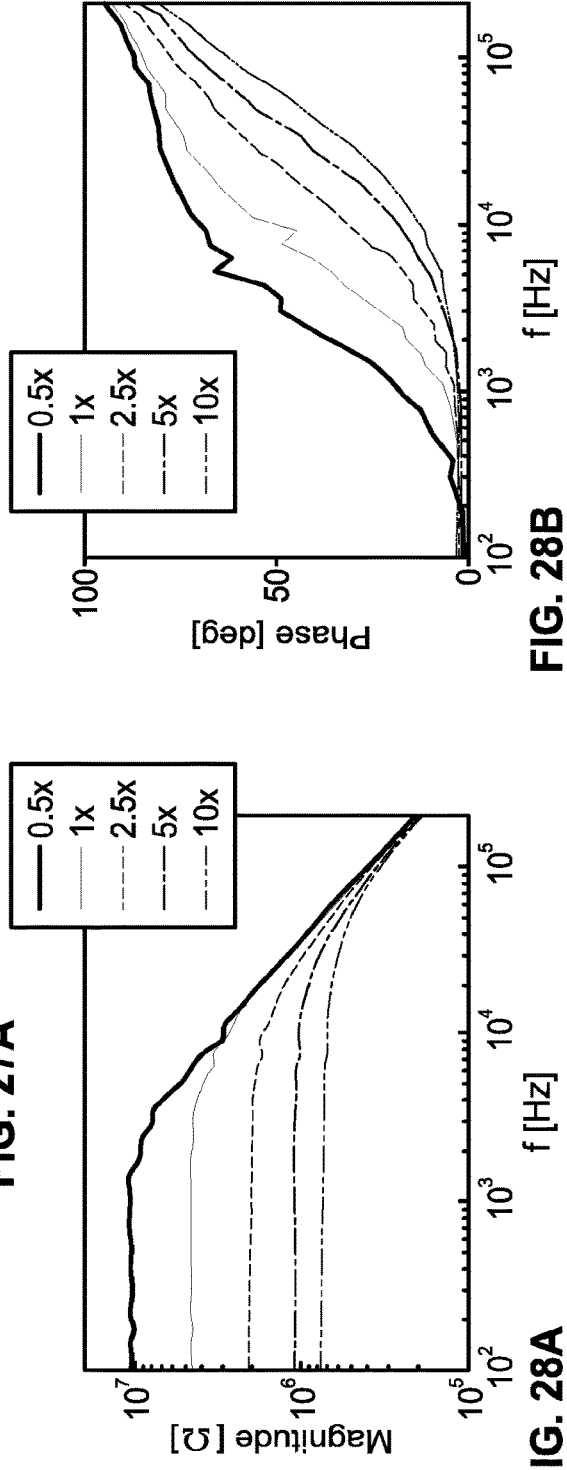
FIG. 28B
FIG. 28A

UNIVERSAL APPROACH FOR DECOUPLING SENSITIVITY AND DYNAMIC RANGE OF A SENSOR

CROSS-REFERENCE TO RELATED APPLICATION(S)

This application is a U.S. National Stage of International Application No. PCT/US2018/022478, filed Mar. 14, 2018, which claims priority to and benefit of U.S. Provisional Patent Application Nos. 62/471,932, filed Mar. 15, 2017 and 62/472,180, filed Mar. 16, 2017, each of which is hereby incorporated by reference herein in its entirety.

GOVERNMENT SUPPORT

This invention was made with government support under grant no. HHSF223201310079 awarded by The Defense Advanced Research Projects Agency (DARPA). The U.S. government has certain rights in the invention.

FIELD OF THE INVENTION

The present invention relates generally to fluidic devices and, more particularly, to fluidic devices incorporating a universal approach for decoupling sensitivity and dynamic range of the fluidic device and methods of making the same and methods of loading and injecting samples into a capture region for measuring and analysis thereof.

BACKGROUND OF THE INVENTION

Sensors are ubiquitous and essential in today's technology. Sensors have three critical parameters that describe their performance: sensitivity, specificity, and dynamic range. Sensitivity is generally defined as the magnitude of response to a step change in the input. Specificity is typically tied to the transduction method itself (e.g., antibody in an immunoassay or ability to remove background noise in an electronic sensor). The dynamic range can be broadly defined as the range of input values over which the sensor provides meaningful data, generally quantitative and accurate data. Although many types of sensors have been developed, many face an inherent relationship between their sensitivity and dynamic range. Intuitively, to measure very small changes (i.e., a very sensitive sensor), a small change in the input needs to effect a large output in order to be measured accurately.

In antibody-based electrical impedance sensors, for example, the sensor consists of an electrode functionalized with antibodies. For a small change in the target analyte to have a large impact, it needs to be bound by a large fraction of the antibodies, which in turn necessitates a small surface area of the electrode. However, with surface area X that meets these requirements, once all the antibodies are bound, the sensor no longer is responsive. Above a certain analyte concentration, more antibodies and therefore a greater electrode surface area are required. Of course with a larger electrode area (e.g., 100×), the same number of analytes that could affect a response in the small electrode will have a far smaller output, reducing sensitivity at low concentrations. On the other hand, a small sensor of area X will saturate at $\frac{1}{100}$ of the bound analyte compared to a sensor of 100× the area. The larger sensor has a larger dynamic range (~100×), but this also means that for much of that range, it is not necessarily a very accurate sensor. This linking of sensitivity and dynamic range has plagued sensing systems, especially biosensors.

Historically, one workaround has been to amplify the signal so that a sensor can detect subtle input changes but still maintain function at the larger input values. This approach requires additional reagents and associated fluid handling, secondary labels, or more complex amplifiers or monitoring schemes. Another improvement consists of converting analog values to frequency, such as through converting capacitance to frequency through having the sensor tune a resonant circuit. For example, a capacitive sensor is placed in a resonant circuit, which changes the resonant frequency as a function of capacitance (e.g., in response to cell attachment or bioanalyte binding). While this method overcomes some of the limitations associated with analog sensors, this approach also links sensor sensitivity to dynamic range through the baseline resonant circuit. The pitfall is that the resonant circuit is designed for optimal performance in a specific, generally narrow, range, and both approaches improve but do not truly decouple sensor sensitivity from the dynamic range as a property of the sensor. More recently, single molecule digital droplet technology has enabled some decoupling of sensitivity from dynamic range by saturating individual droplets containing a single target analyte with the output of an amplification reaction (e.g., PCR in the case of DNA detection) and generating as many droplets as required to achieve the desired dynamic range. However, this approach is limited to only a small subset of possible sensors since most cannot convert the target analyte or property into discrete droplets for signal amplification (e.g., sample mass, capacitance, etc.).

Detection and quantification of biomolecules is a central topic in research and clinical diagnostics. However, current assays are expensive, have a long sample-to-answer time and a long hands-on time. These limitations suggest the need for a new kind of diagnostic device. Fluidics (e.g., nanofluidics, microfluidics, macrofluidics, etc.) has proven to be a promising technology to miniaturize and integrate laboratory procedures. Such fluidic devices that integrate sample handling and analysis inside a miniaturized chip is often referred to as 'lab-on-a-chip'. Because relevant volumes in fluidic systems (e.g., microfluidic, nanofluidic) are small, for example, below the microliter range, the volume of precious samples and costly reagents are reduced substantially compared to conventional methods. Moreover, reaction times are shortened enabling much faster assays. Furthermore, multiple manufacturing methods have been demonstrated to enable the creation of microfluidic devices in a scalable way to reduce the cost per device thus making the applications of microfluidic devices commercially interesting.

A wide range of fluidic sensors have been demonstrated with varying underlying mechanisms for biomolecule immobilization and detection. Electrochemical impedance spectroscopy/sensing (EIS) is an attractive readout modality because of its simple operation, low cost, and potential for high sensitivity without the use of labels. In general, impedance biosensors use electrodes that are functionalized by biorecognition elements that can bind with the analyte of interest. When antibodies are employed as biorecognition element, such sensor is called an impedance immunosensor. Any analyte bound to the antibodies on the electrode surface will change the impedance of the electrode-electrolyte interface which is subsequently measured to quantify the concentration of the protein present in the sample. A major benefit of this detection mechanism is the ability to perform a label-free assay which shortens the assay time and costs.

Fluidic chips with integrated electrodes that incorporate impedance measurements to detect biomolecules are an active field of research. However, in the classical design of this sensor, the surface area of the electrode limits the number of receptors sites and thus the dynamic range of the sensor. Furthermore, the size of the electrodes influences the sensitivity, since a larger electrode surface results in a smaller change of impedance upon binding. The sensitivity and dynamic range of the sensor are thus coupled and inversely related to each other. That is, sensors with a high sensitivity have a small dynamic range, while sensors with a large dynamic range have a low sensitivity. This trade-off requires the user to either have an estimation of the concentration of the target of interest beforehand or make several dilutions of the sample in order to cover a wide range of concentrations. Ideally, the dynamic range and sensitivity would be decoupled.

The present disclosure is directed at providing a fluidic sensor that solves the above and other needs.

SUMMARY OF THE INVENTION

The present disclosure provides devices (e.g., microfluidic devices, sensors, etc.) and methods that decouple the sensitivity and dynamic range by moving from traditional two-dimensional sensors to a three-dimensional sensor (e.g., a sensor including a three-dimensional matrix of receptors therein configured to bond with an analyte of interest). In such sensors, the cross sectional area of the capture region correlates with the sensitivity, while the length of the region correlates with dynamic range. Since these geometries are independent from one another, sensitivity and dynamic range can be decoupled. According to some implementations, this approach is suitable for label free sensing, thereby reducing the number of assay steps and reagents required.

According to some implementations, the decoupling of sensitivity and dynamic range using geometry results in a saturation of parts of the sensor as the analyte enters the sensor region.

According to some implementations, a four electrode sensor setup is used to generate a current between a pair of outer electrodes and pick up the potential between a pair of inner electrodes, thereby bypassing surface effects on the electrode.

According to some implementations, using NSA as a conjugating agent (e.g., in the capture material, capture hydrogel, etc.) leads to a zero-length conjugation. This is compared to using biotin-streptavidin, which would introduce two large proteins in between the antibody and monomer. This way the relative change of impedance upon binding is increased.

The present disclosure provides devices and methods that decouple the sensitivity and dynamic range of impedance immunosensors. This work presents the development of a robust microfluidic platform that aims at demonstrating decoupling the sensitivity and dynamic range of an impedance immunosensor by capturing the biomolecules in a 3D matrix and separating the detection electrodes from the binding sites. The sensitivity of this sensor is in theory determined by the cross sectional area of the microfluidic channel in which the biomolecules are captured while the length of this channel determines the dynamic range. A model using circuit analysis is presented to describe the decoupling and linearity of the sensor response. The developed platform includes electrokinetic sample handling to dispense small volumes of sample into the chip using electrophoresis, fabrication of hydrogels conjugated with antibodies (e.g., capture material) to capture specific proteins, and integrated electrodes for performing impedance spectroscopy inside the microfluidic device.

Apart of the potential desirable property of a decoupled sensitivity and dynamic range, this prototype also functions as a first step towards developing an easy to use, bench top diagnostic platform for fast sample analysis. The microfluidic devices are designed for low-cost scalable production processes.

The present disclosure further includes novel concepts of sensor design that decouple sensitivity and dynamic range. The principle relies on the ability to sequentially measure small, highly sensitive regions of a sensor and repeat these regions to achieve the desired dynamic range and maintain a constant high sensitivity until saturation. Additionally, the saturation of one region removes some of the input from the following region, reducing the input value until what is left is within range of a single sensor element. This has the effect of linearizing sensors, which are inherently non-linear due to saturation at the upper end of the range and sensor noise at the lower end. Through a serial linkage of individual high-sensitivity sensing regions coupled with serial exposure to the input only after the preceding sensing region begin to saturate, we achieve theoretical high sensitivity that is relatively constant across an arbitrary range of inputs. We demonstrate an application for electrical impedance label-free sensing of proteins, but this approach can be applied to additional biological and non-biological sensing or transduction modalities.

According to some implementations of the present disclosure, as a first example, mass could be sensed by having a stack of identical high-sensitivity sensors (e.g., piezo resonators like those used in many precision microbalances), each suspended above the other using fine springs, pneumatics, hinges, or other approach with a saturating behavior. As the mass of an object placed on the sensor stack increases, the sensors will serially saturate, each providing a unit of sensor input while the unsaturated sensor provides analog information within its measurement range.

According to some implementations of the present disclosure, as a second example, electrical capacitance could be measured using serial capacitive sensors separated by a resistive element. As the first sensor saturates, the signal transitions to the second sensor and so on, enabling measurement at the sensitivity of a single sensor but across the necessary dynamic range. This could consist of a linear arrangement of detection capacitive sensors that get sequentially used until saturation, removing some of the input, until one sensor is capable of an accurate readout.

According to some implementations of the present disclosure, in a third example and as we show in the experimental example below, capacitive and resistive components of proteins can be measured in a single 3D sensor that sequentially saturates infinitely thin sections of the sensor. The cross sectional area directly affects the sensitivity while the depth of the sensor determines dynamic range.

According to some implementations of the present disclosure, a microfluidic device includes a microfluidic layer, a capture material, and an electronics layer. The microfluidic layer includes a main channel and a pair of sample channels fluidly coupled to the main channel. The pair of sample channels is configured to receive and introduce a sample material into the device. The sample material includes an analyte. The capture material is positioned in a portion of the main channel that is spaced from the pair of sample channels. The capture material has a three-dimensional matrix of receptors therein configured to bond with the analyte. The electronics layer includes electrodes configured to measure an electrical resistance through a portion of the capture material.

According to some implementations of the present disclosure, a microfluidic device for measuring a concentration of an analyte in a sample material includes a microfluidic layer, a capture hydrogel, and an electronics layer. The microfluidic layer includes a main channel and a pair of sample channels fluidly coupled to the main channel. A first of the pair of sample channels extends from a first side of the main channel and a second of the pair of sample channels extends from a second opposing side of the main channel. The pair of sample channels is configured to receive and introduce a sample material into the device. The sample material includes an analyte. The capture hydrogel is positioned in a portion of the main channel that is spaced from the pair of sample channels. The capture hydrogel has a three-dimensional matrix of receptors therein configured to bond with the analyte. The capture hydrogel has a length that is associated with a dynamic range of the microfluidic device and a cross-sectional area that is associated with a sensitivity of the microfluidic device. The electronics layer includes an inner pair of electrodes and an outer pair of electrodes. The inner pair of electrodes is configured to measure an electrical resistance through a portion of the capture material responsive to a current being applied to the outer pair of electrodes.

According to some implementations of the present disclosure, a fluidic device includes a fluidic layer, a capture material, and an electronics layer, the fluidic layer includes a main channel and a pair of sample channels fluidly coupled to the main channel. The pair of sample channels is configured to receive and introduce a sample material into the device. The sample material includes an analyte. The capture material is positioned in a portion of the main channel that is spaced from the pair of sample channels. The capture material has a three-dimensional matrix of receptors therein configured to bond with the analyte. The capture material has a length that is associated with a dynamic range of the fluidic device and a cross-sectional area that is associated with a sensitivity of the fluidic device. The electronics layer includes electrodes configured to measure an electrical resistance through a portion of the capture material.

According to some implementations of the present disclosure, a fluidic device for measuring a concentration of an analyte in a sample material includes a fluidic layer, a capture hydrogel, and an electronics layer. The fluidic layer includes a main channel and a pair of sample channels fluidly coupled to the main channel. A first of the pair of sample channels extends from a first side of the main channel and a second of the pair of sample channels extends from a second opposing side of the main channel. The pair of sample channels is configured to receive and introduce a sample material into the device. The sample material includes an analyte. The capture hydrogel is positioned in a portion of the main channel that is spaced from the pair of sample channels. The capture hydrogel has a three-dimensional matrix of receptors therein configured to bond with the analyte. The capture hydrogel has a length that is associated with a dynamic range of the fluidic device and a cross-sectional area that is associated with a sensitivity of the fluidic device. The electronics layer includes an inner pair of electrodes and an outer pair of electrodes. The inner pair of electrodes is configured to measure an electrical resistance through a portion of the capture material responsive to a current being applied to the outer pair of electrodes.

According to some implementations of the present disclosure, a fluidic device includes a fluidic layer, a capture material, and an electronics layer. The fluidic layer includes a main channel, a pair of sample channels fluidly coupled to the main channel, and two or more electrode channels fluidly coupled to the main channel. The pair of sample channels is configured to receive and introduce a sample material into the device, the sample material including an analyte. The capture material is positioned in a portion of the main channel that is spaced from the pair of sample channels. The capture material has a three-dimensional matrix of receptors therein configured to bond with the analyte. The electronics layer includes electrodes positioned at least partially within the two or more electrode channels such that the electrodes are configured to measure an electrical resistance through a portion of the capture material.

According to some implementations of the present disclosure, a fluidic device for measuring a concentration of a target in a sample material includes a fluidic layer, acapture hydrogel, and an electronics layer. The fluidic layer includes a main channel and sample channels fluidly coupled to the main channel. A first of the sample channels extends from a first side of the main channel and a second of the sample channels extends from a second opposing side of the main channel. The sample channels are configured to receive and introduce a sample material into the device. The sample material includes a target. The capture hydrogel is positioned in a portion of the main channel that is spaced from the sample channels. The capture hydrogel has a three-dimensional matrix of receptors therein configured to bond with the target. The capture hydrogel has a length that is associated with a dynamic range of the fluidic device and a cross-sectional area that is associated with a sensitivity of the fluidic device. The electronics layer includes electrodes configured to measure an electrical resistance through a portion of the capture material.

Additional aspects of the present disclosure will be apparent to those of ordinary skill in the art in view of the detailed description of various embodiments, which is made with reference to the drawings, a brief description of which is provided below.

BRIEF DESCRIPTION OF THE DRAWINGS

FIG. 15A illustrates a hot-embossing of microfluidics portion of a manufacturing process including, from top to bottom, put a piece of COP or PC together with the mold in the hot press, hot emboss the polymer in the mold and remove from the mold, apply solvent to the at surfaces of the feature side of the microfluidics to create a soft layer for bonding;

FIG. 15B illustrates an electrode portion of the manufacturing process of FIG. 15A including, from top to bottom, starting with a clean wafer of COP or PC, evaporate a thin adhesion layer of titanium and a layer of gold, spin coat photoresist, expose photoresist trough a mask with the pattern of the electrodes and develop, etch the gold and titanium and finally wash the remaining photoresist on the electrodes;

FIG. 15C illustrates a bonding portion of the manufacturing process of FIG. 15A including align the microfluidics and electrodes, wick in solvent and laminate at 137° C.;

FIG. 16A illustrates a top schematic view of a hydrogel positioning process;

FIG. 16B illustrates a perspective view of a hydrogel positioning process;

FIG. 25A illustrates an Electropherogram of fluorescent labeled anti-BSA for four electric field strengths, measured at the beginning of the capture gel, after electrokinetically injecting at t=0;

FIG. 25B illustrates sample migration velocities, calculated by dividing the peak times by the traveled distance (5.9 mm) and a linear fit indicating the electrophoretic mobility;

FIG. 26A illustrates a single injected sample plug moving through a channel;

FIG. 26B is a plot of an associated concentration profile of the sample plug of FIG. 26A;

FIG. 27A illustrates capturing of proteins in the hydrogel where fluorescent images of the capture gel after 0, 4, 7, 10 and 13 injections are shown with a line indicating the start of the capture gel;

FIG. 27B illustrates associated intensity profiles of the fluorescent images of FIG. 27A normalized to the intensity profile before injection;

FIG. 28A illustrates impedance magnitude for five concentrations of tris-glycine (TG) buffer;

FIG. 28B illustrates impedance phase for the five concentrations of tris-glycine (TG) buffer of FIG. 28A;

Figure 1:
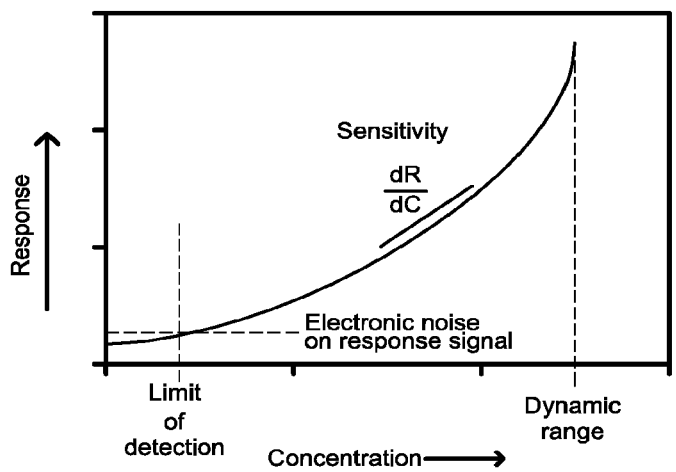
FIG. 1 illustrates a response curve of a biosensor, indicating the limit of detection, sensitivity and dynamic range.

While the present disclosure is susceptible to various modifications and alternative forms, specific implementations and embodiments have been shown by way of example in the drawings and will be described in detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

LIST OF SYMBOLS USED THROUGHOUT IN DESCRIPTION $\varepsilon$—Permittivity [F/m]
$\eta$—Viscosity [Pass]
$\lambda_D$—Debeye-Hunckel length [m]
J—Diffusion flux [mol/m$^2$s]
$\mu$—Electrokinetic mobility [m$^2$/V s]
$\rho$—density [kg/m$^3$]
$\sigma$—Conductivity [S/m]
$\phi$—Electric potential in the double layer [V]
$\zeta$—Zeta-potential [V]
C—Capacitance [F]
c—Concentration [mg/ml] or [M]
D—Diffusion coefficient [m$^2$/s]
$E_x$—Applied electric field in one dimension [V/cm]
$f_v$—Drag coefficient [kg/s]
h—height [m]
I—Fluorescent intensity [a.u.]
i—Electrical current [A]
L—Length [m]
m—mass [kg]
P—Pressure [Pa]
q—Electrical charge [C]
R—Electrical resistance [$\Omega$]
T—Temperature [° C.]
t—Time [s]
U—Measured or applied potential [V]
U—Velocity, fluid velocity in electroosmosis and particle velocity in electrophoresis [m/s]
v—volume [kg]
$V_n$—Measured or applied potential in reservoir n [V]
w—width [in]
x—Spacial coordinate over the length of the channel [m]
z—Spacial coordinate perpendicular to a surface [m]

DETAILED DESCRIPTION

Biosensors

The purpose of a biosensor is to detect and to quantify the presence of a biomolecule of interest, which is referred to as an analyte. Many different concepts of biosensors have been reported in literature and are commercially available. In general, a biosensor can be split up into two parts: a biological recognition element and a transducer. The biological recognition element interacts with the analyte whereas the transducer transforms the interaction between the bio-recognition element and the analyte into a measurable signal.

Affinity biosensors are a class of biosensors defined as analytical devices composed of a biological recognition element (e.g., receptors), such as, for example, an antibody, receptor protein, biomimetic material, DNA interfaced to a signal transducer, one or more proteins (e.g., one or more transcription factors or fragments thereof, one or more lectins or fragments thereof, one or more antibodies or fragments thereof, one or more short peptides or fragments thereof, or any combination thereof), one or more lipids or fragments thereof, one or more cells or fragments thereof, bacteria or fragments thereof, one or more viruses or fragments thereof, one or more small chemical molecules or fragments thereof, one or more carbohydrates or fragments thereof, one or more glycosylated molecules or fragments thereof, or any combination thereof, which together relate the concentration of an analyte to a measurable electronic signal. Affinity refers to the specificity of the binding between the biological recognition element and analyte, such as the binding between an antigen-antibody pair or to complementary single-stranded DNA. Antibodies demonstrate high affinity and are both versatile and commercially well available and are therefore the most widely employed biological recognition elements in affinity based biosensors. Affinity biosensors that employ antibodies as biorecognition element are called immunosensors.

Transducers can be classified based on their underlying physical working mechanism. Common types of transducers are optical, magnetic, mechanical and electronic transducers. The workhorse for biosensing in the typical laboratory setting, the enzyme-linked immunosorbent assay (ELISA) is an affinity biosensor that uses an optical transducer. This biosensor relies on a specific antibody that captures the analyte of interest on a surface. After the binding step, an enzyme conjugated to an antibody specific to the analyte is bound to the captured analyte. This enzyme is thereafter able to produce a colorimetric signal in the presence of the enzyme's substrate. Although this method has proven to be extremely useful in the laboratory, it has several downsides, the main ones being the long hands-on time and sample-to-answer time due to multiple labeling and washing steps.

Electronic transducers show great potential for applications where minimizing costs and size are important, since electrical transducers do not contain expensive optical or magnetic components and contain no moving mechanical parts. Impedance biosensors are a class of biosensors that operate by applying a small sinusoidal voltage to the biological recognition element, and measuring the resulting sinusoidal current. Using small perturbations leads to an almost linear current response with a certain amplitude and phase shift, which can be related to the input voltage at a range of frequencies. This is called electrochemical impedance spectroscopy.

An immunosensor that employs electrochemical impedance spectroscopy as a transducer mechanism is called impedance immunosensor. A typical example of an impedance immunosensor is an electrode surface with immobilized antibodies. The analyte can bind with the immobilized antibodies, upon which the electrical properties of the surface change, resulting in a different impedance at the surface. Consequently, the measured impedance can be related to the amount of bound analyte. Impedance immunosensors allow the performing of measurements without the need of secondary antibodies for labeling, which is called label-free detection. The major advantages of label-free detection are decreased costs per assay due to reduced use of reagents and a decrease in assay time since it eliminates additional time consuming washing and labeling steps. Furthermore, label-free detection allows the performing of real-time measurements. Impedance immunosensors are for these reasons an increasing topic of interest in research and industry and the subject of this work.

Sensitivity and Dynamic Range

A biosensor is generally characterized by its sensitivity and dynamic range. The sensitivity of a sensor is defined as the derivative of the response signal (R) with respect to the analyte concentration (C), which is illustrated in FIG. 1. The dynamic range of a biosensor is defined as the range between the largest measurable target concentration and the lowest detectable concentration, and is this is determined by either the number of binding sites or the limit of the instrumentation. The lowest detectable concentration is also called limit of detection (LOD). The LOD in impedance immunosensors is the target concentration required to induce the minimally-detectable change in impedance based on the intrinsic electronic noise of the impedance readout, Also defined as the lowest statistically significant concentration which is often 3× the noise background. The LOD is illustrated in FIG. 1.

Figure 2A:
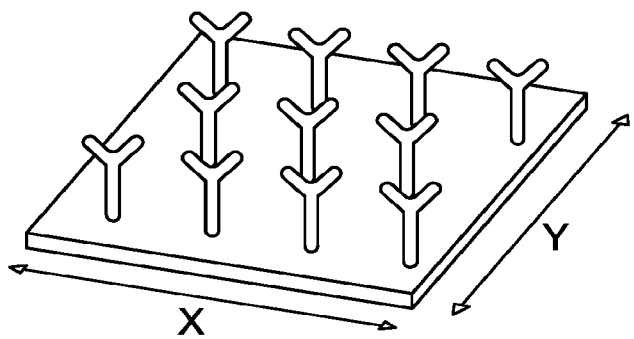
FIG. 2A illustrates a schematic setup of a 2D impedance immunosensor showing a functionalized electrode surface.
Figure 2B:
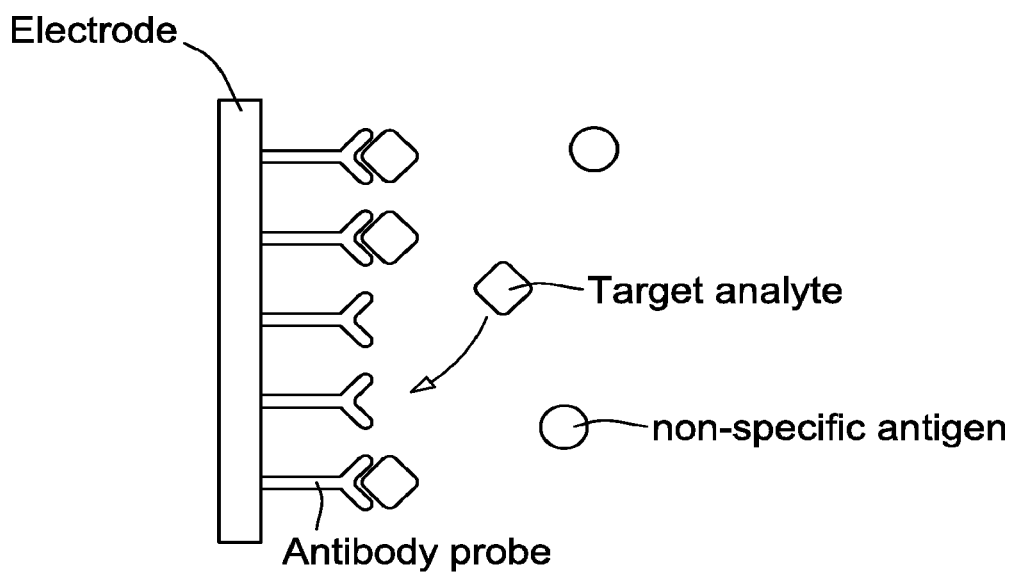
FIG. 2B is a cross sectional view of a capture process using the 2D impedance immunosensor of FIG. 2A.

In 2D impedance immunosensors, shown in FIGS. 2A and 2B, the number of binding sites is limited by the surface area of the electrode. The sensor is saturated when all binding sites are occupied.

Increasing the electrode surface area therefore results in a larger dynamic range. Larger electrodes furthermore reduce the noise on the readout system. However, the larger an electrode gets, the smaller the relative change in impedance is upon binding, thus reducing the sensitivity. This trade-off demonstrates how the sensitivity and dynamic range in a 2D impedance immunosensor are coupled and inversely related to each other.

Figure 3A:
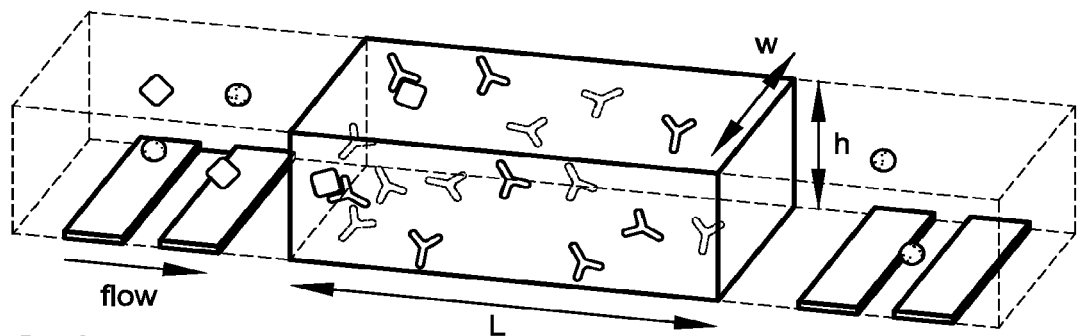
FIG. 3A illustrates a schematic setup of a 3D impedance immunosensor including a capture gel.
Figure 3B:
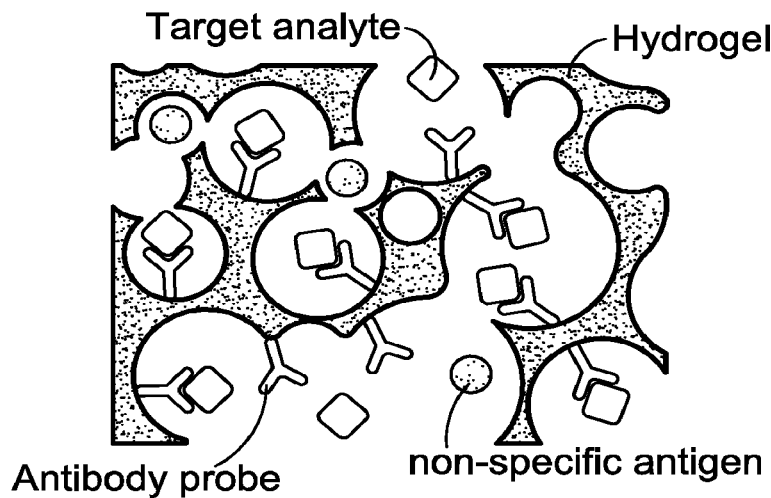
FIG. 3B is a cross sectional view of a capture process using the 3D impedance immunosensor of FIG. 3A.

Three-dimensional (3D) structures offer increased surface-area-to-volume ratio compared to planar immobilization, resulting in an increase in the number of immobilization sites and a decrease in the diffusion length between the probe and the analyte. It has been estimated that a 3D matrix can provide approximately a 100-1000 fold increase in binding sites, which greatly increases the dynamic range of the sensor. The capturing mechanism in a 3D matrix is illustrated in FIGS. 3A and 3B. As can be seen, the increased surface-area-to-volume ratio allows more binding inside the immobilization volume. Furthermore, the use of a 30 matrix for immobilization makes it possible to decouple the electrodes from the hydrogel (e.g., capture material). Large electrodes can be placed outside of the hydrogel region to reduce electronic noise, while the hydrogel can keep a small cross sectional area in order to increase the sensitivity.

The implementation of the present disclosure shown in, for example, FIGS. 3A and 3B decouples the sensitivity and dynamic range of the sensor by immobilizing probes in a 3D matrix (e.g., a three-dimensional hydrogel matrix material/solution/gel). Sensing is performed by measuring the impedance through the 3D matrix with electrodes that are positioned outside of the 3D matrix. The cross-sectional area of the 3D matrix determines the sensitivity while the length of the 3D matrix determines the dynamic range. FIGS. 3A and 3B schematically illustrates how the 3D matrix captures target analyte. L indicates the length of the matrix, which determines the dynamic range of the sensor and X by Y indicate the surface area of the matrix which determine the sensitivity of the sensor. A 3D matrix enables saturation of the sensor at the inlet, thereby increasing signal with a small input, thus increasing sensitivity. The diffusion kinetics of a 3D sensor are fast compared to 2D sensors, enabling faster, more efficient analyte capture.

Figure 4A:
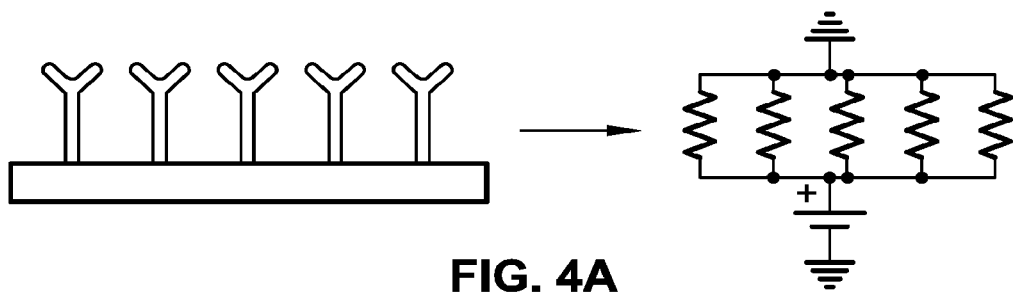
FIG. 4A illustrates an electrical circuit analogy of the 2D impedance immunosensor of FIG. 2A.
Figure 4B:
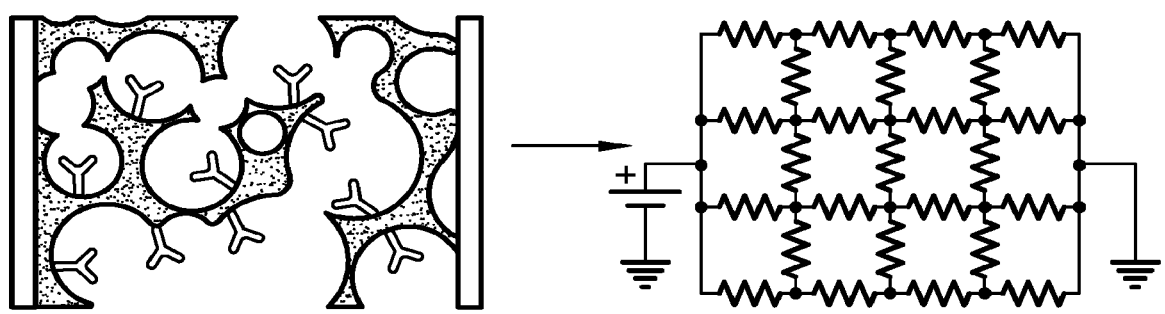
FIG. 4B illustrates an electrical circuit analogy of the 3D impedance immunosensor of FIG. 3A.

In order to demonstrate how 3D structures decouple the dynamic range and sensitivity in immunosensors, an analogy can be made with electrical circuits, shown in FIGS. 4A and 4B. In very simplified form, the 2D functionalized electrode can be represented as a number of parallel resistors, while the 3D functionalized hydrogel (e.g., capture material) can be thought of as a grid of resistors. This dramatically simplifies the physics of the system, but gives insight into the relation between dynamic range and sensitivity of the immunosensors.

Figure 5:
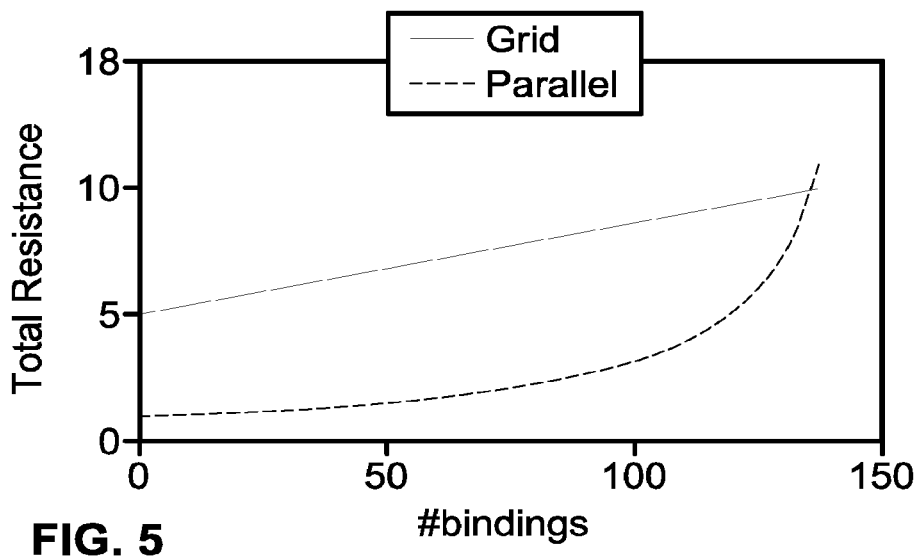
FIG. 5 illustrates a response curve of 137 parallel resistors and 137 resistors in a 4×20 grid.

Each immobilized antibody is represented by a resistor with a certain resistance, and upon binding with analyte, this resistance will increase. The total number of resistors indicates the number of binding sites, and thus the dynamic range of the sensor. FIG. 5 shows the response curves of 137 parallel resistors and 137 resistors in a 4×20 grid. These curves indicate the equivalent resistance of both networks of resistors while sequentially increasing the resistances of each individual resistor from the left to the right. As can be seen, the response curve of the parallel resistors is exponential, which means that the sensitivity, i.e. the slope of the response curve is low for a small number of binding events and high when the sensor is nearly saturated. This demonstrates how sensors with a larger dynamic range have a poor low concentration sensitivity, and these two properties are thus coupled. In contrast, the response curve of the grid resistor demonstrates a near-constant slope over its entire range; the sensitivity is not dependent on the dynamic range and these two properties are thus decoupled.

Figure 6A:
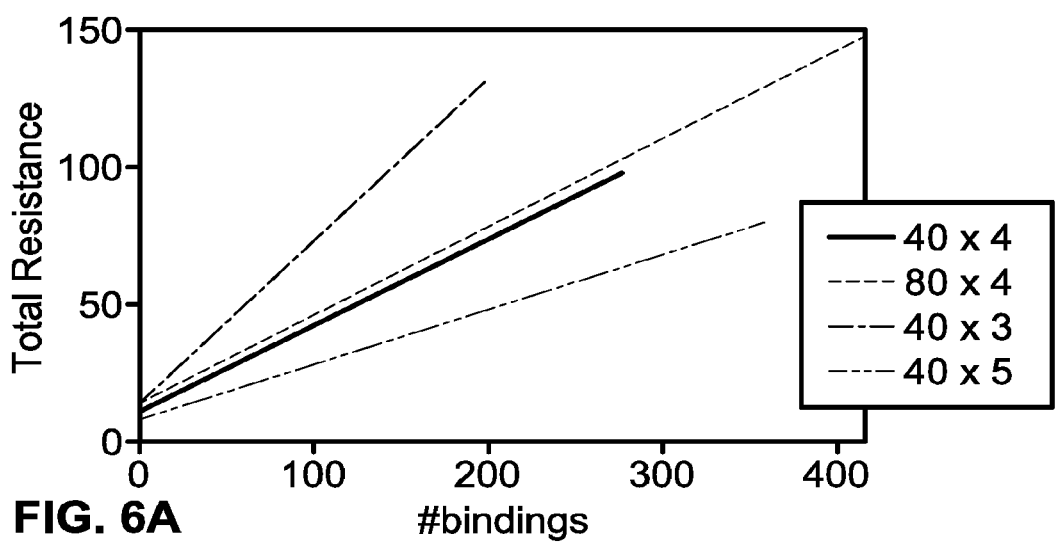
FIG. 6A illustrates a response curve for varying resistor grids, L x A, where L indicates the number of resistors in the horizontal direction, equivalent to the length of the hydrogel, and A indicates the vertical direction, equivalent to the cross sectional area of the hydrogel.
Figure 6B:
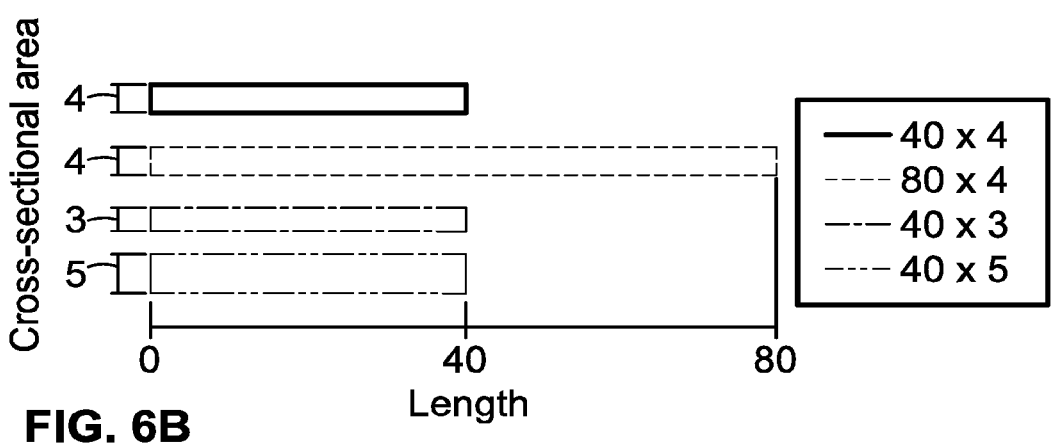
FIG. 6B illustrates shapes of the four corresponding hydrogels in FIG. 6A.
Figure 7A:
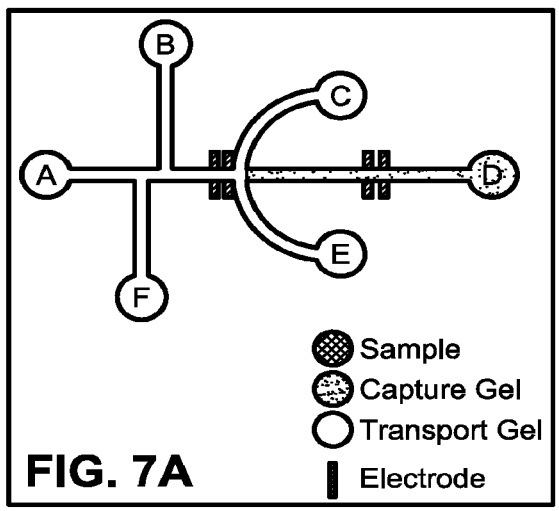
FIG. 7A illustrates a first step in operating a microfluidic sensor including positioning a capture gel between electrodes.
Figure 7B:
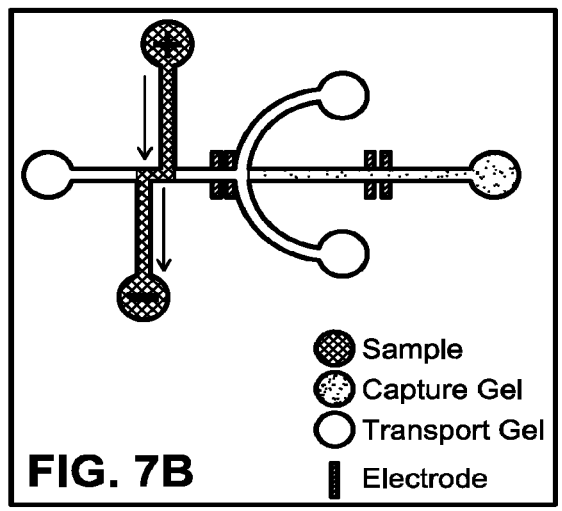
FIG. 7B illustrates a second step in operating the microfluidic sensor of FIG. 7A including loading a sample.
Figure 7C:
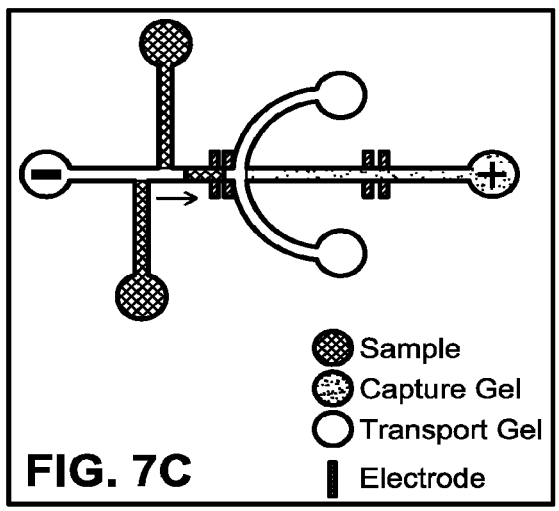
FIG. 7C illustrates a third step in operating the microfluidic sensor of FIG. 7A including injecting a quantified amount of sample towards a sensing region.
Figure 7D:
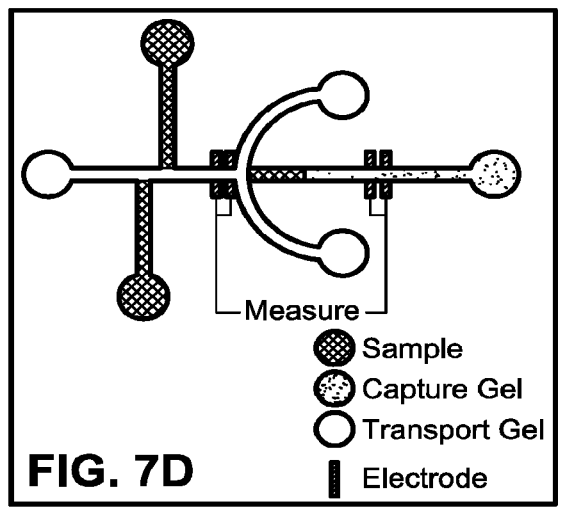
FIG. 7D illustrates a fourth step in operating the microfluidic sensor of FIG. 7A including capturing an analyte of interest and measuring a corresponding change in impedance upon capturing.

FIGS. 6A and 6B shows response curves for 4 different setups of resistor grids. The number of resistors in the horizontal direction can be seen as an analogy to the length of the channel, L, whereas the number of resistors in the vertical direction represents the channel cross-sectional area, A. As can be seen, increasing the number of resistors in the horizontal direction leads to an increase in binding sites, but does not change the slope of the response curve. This indicates that increasing the channel length does not affect the sensitivity but increases the dynamic range. Furthermore, decreasing the number of resistors in the vertical direction results in a steeper slope, which indicates that decreasing the channel cross-sectional area results in an increased sensitivity. This result illustrates that the sensitivity and dynamic range are theoretically decoupled in a 3D impedance immunosensor and can be controlled by two parameters, the channel length and cross-sectional area.

Although this example demonstrates the mechanism behind the decoupling, it should be noted that the parallel and grid resistor models are very idealized and simplified; however, this gives an idea about how to model the sensor response. As immobilized proteins also have certain capacitive properties, the model can probably be improved by replacing each resistor with a parallel resistor and capacitor. This model can then be fitted through measurement data to obtain the values for the resistance and capacitance of each binding site before and after binding.

A theoretical rationale for decoupling dynamic range from sensitivity of a sensor is now described according to some implementations of the present disclosure. An infinitely thin cross-section of a 2D sensor is represented as a parallel resistor circuit, with each resistor representing a single capture site. The equivalent resistance (Req2D) for the sensor is described by equation 1.1:

$$Req2D = \left(\frac{x}{Ru} + \frac{C-x}{Rb}\right)^{-1}$$

Where x is the number of unbound capture sites, C is the total number of capture sites, Ru is the resistance of the unbound capture site, and Rb is the resistance of the bound capture site. This equation results in an exponentially increasing resistance as the sensor captures more target molecules. The maximum sensor change (ratio of saturated sensor to empty sensor) as the capture sites bind the targets can be expressed as described by equation 1.2:

$$Req2D \text{ change} = \left(\frac{C}{Rb} \bigg/ \frac{C}{Ru}\right)^{-1} = \frac{Rb}{Ru}$$

We represent a 3D sensor as a stack of single capture site 2D arrays. This is possible due to the assumption that the binding of a single target molecule to one capture site will have only a relatively small impact on sensors with many binding sites, enabling us to simplify the grid of resistors shown in FIGS. 4A and 4B as a single 2D array that is directly proportionally greater in resistance than a single 2D layer. The number of 2D arrays of molecular layers of capture sites (N) are calculated as the physical sensor length divided by number of capture sites per unit distance as described by equation 1.3 below. In the case of homogenous sensors, such as antibodies immobilized randomly in a gel, the number of 2D capture site arrays (N) of the 2D array will equal the density along the length of the sensor.

$$N = \frac{length}{x}$$

Additionally, target molecules can be captured non-uniformly in the sensor, starting at the input side. Target molecules will be more likely to bind to the earlier unbound capture sites until a given 2D slice nears saturation. Incorporating the length of the sensor and assuming a homogenous capture site distribution, the equivalent resistance (Req3D) for this sensor is described by equation 1.4:

$$Req3D = \sum_{n=1}^{N}\left(\frac{x}{Ru_n} + \frac{C-x}{Rb_n}\right)^{-1}$$

This equation 1.4 sums the equivalent resistance of each 2D capture site array across the length of the sensor. As the fraction of bound capture sites increases, the simulation results shown in FIG. 6A demonstrate a linear relationship between number of bound sites and the equivalent resistance due to the summation of the 2D capture site arrays and essentially converting the array of parallel resistors into a single equivalent resistor network that can simply be summed. The slope of the response of a 3D sensor, as shown in FIG. 6A, depends on the cross sectional area of the sensor since a small number of unbound, and the dynamic range of the sensor is a function of the length of the sensor. Since the Req3D response is linear, the addition of capture sites along the length of the sensor does not impact the sensitivity and only extends the number of capture sites to increase the dynamic range.

The maximum change in Req3D can be expressed as described by equation 1.5:

$$Req3D \text{ change} = \sum_{n=1}^{N} \frac{Rb_n}{Ru_n}$$

This again demonstrates that the length of a sensor will arbitrarily extend the dynamic range without impacting sensitivity of each 2D capture site array. From equation 1.5, one can see that to maximize the Req3D change for a fixed ratio of Rb to Ru, the sensor should be long. To achieve maximum sensor change for each 2D slice, the number of unbound capture sites x should be minimized (saturated 2D sensor). Therefore, to measure a low number of target molecules, one should reduce the number of total capture sites C per 2D slice to a minimum, ideally single molecules. This suggests that the decoupling strategy and sensitivity in particular is improved by decreasing the sensor cross-section size scales, ideally to the size (e.g., diameter, maximum width, maximum height, maximum cross-sectional area, etc.) of the targets (e.g., about one nm diameter to about ten nm diameter for many biological targets, about twenty nm diameter to about five hundred nm diameter for viruses, and in the micron range (e.g., about one micrometer diameter to about 950 micrometers) of diameter for bacteria and other cells). Microfluidic and nanofluidic geometries offer the appropriate scales for detection of typical biological target analytes of interest.

Sensor Concept

The proposed concept and operating principle to test the hypothesis whether the three-dimensional (3D) sensor design (e.g., 3D microfluidic devices) decouples the sensitivity and dynamic range is illustrated in FIGS. 7A-7D. As can be seen, the sensor consists of 6 access ports. First, the entire chip is filled with a transport gel without any binding sites, and a capture gel with immobilized antibodies (blue) is injected from the rightmost inlet and positioned between the electrodes indicated in FIG. 7A. Next, a sample (red) is loaded into the device and consecutively injected towards the capture area using electrophoresis. The analyte of interest in the sample is captured by the antibodies in the capture gel and the change in impedance is measured between the electrodes that are in contact with the microchannel. This process is repeated several times for channels with varying cross sectional areas to study how the geometry of the channel affects the sensitivity and dynamic range of the sensor.

Hydrogel Chemistry

The main purpose of the hydrogel is to capture the analytes and provide a biocompatible environment for the proteins. Polyacrylamide, PEG diacrylate gel, chitosan and agarose are popular hydrogels for protein immobilization purposes. For the purpose of this project, polyacrylamide is selected as the preferred hydrogel because of its possibility to linearly polymerize, creating viscous and injectable hydrogels, and because modifications of polyacrylamide gels and conjugation of biomacromolecules to polyacrylamide gels are well described in the literature. The hydrogel should contain antibodies that function as probes to catch target analyte. These antibodies can be conjugated to the gel by several methods. The most widely employed immobilization pair in biosensors is the streptavidin-biotin pair. Streptavidin, a protein, and biotin, water-soluble vitamin B, have the ability to form one of the strongest non-covalent bonds known in nature. Many biotin-modified (biotinylated) proteins, peptides and DNA strands modified with biotin are commercially available. Streptavidin modified monomers, such as streptavidin acrylamide can be polymerized in the presence of the biotinylated antibodies to create a functionalized hydrogel in a single step. Alternatively, streptavidin-acrylamide can be copolymerized into a polyacrylamide hydrogel, and later activated by flowing biotinylated antibodies through this streptavidin-hydrogel before use. Both methods have been demonstrated inside microfluidic chips.

Although this is a well-known and widely employed method to conjugate antibodies to hydrogel, it has several downsides. First of all, the modified antibodies and monomers are significantly more expensive than their native forms, which might not be a problem in a research setting, but will increase the cost per assay, which is an important aspect for commercialization. Secondly, the biotin-streptavidin conjugate has a significant size (52.8 kDa) and substantial associated capacitive properties while bound inside the hydrogel matrix. The sensitivity of the sensor is determined by how well a relative change in impedance can be detected. The immobilized antibody and biotin-streptavidin coupling without bound analyte contribute significantly to the total possible impedance signal, which might obscure the relative change in impedance upon binding with the analyte.

Figure 8:
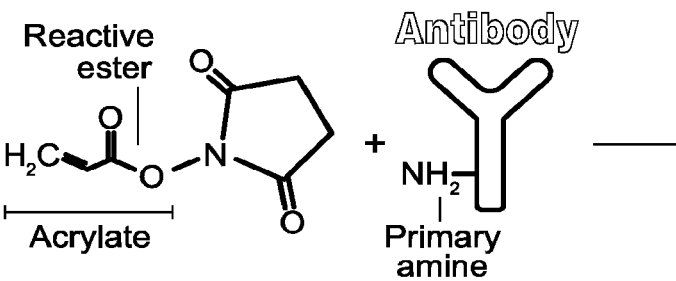
FIG. 8 illustrates a modification of an antibody with NSA.
Figure 9A:
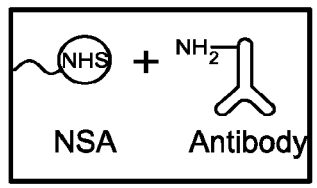
FIG. 9A illustrates a hydrogel functionalization step of incubating an antibody with NSA to introduce a vinyl group.
Figure 9B:
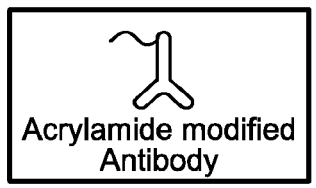
FIG. 9B illustrates a hydrogel functionalization step of a resulting monomer modified antibody.
Figure 9C:
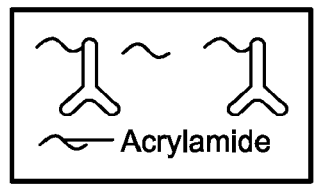
FIG. 9C illustrates a hydrogel functionalization step of mixing monomer modified antibodies in an acrylamide monomer solution.
Figure 9D:
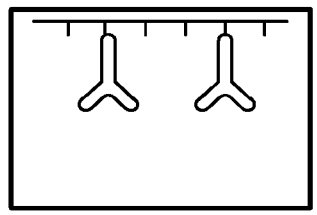
FIG. 9D illustrates a hydrogel functionalization step of a polymerizing the monomer solution in the absence of a cross-linker to create a functionalized, viscous polyacrylamide capture gel.
Figure 9E:
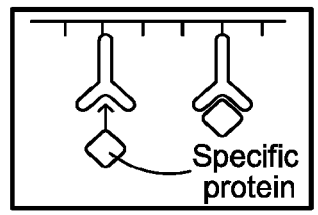
FIG. 9E illustrates a hydrogel functionalization step of a capturing specific proteins using this capture gel.

For this reason, it is favorable to conjugate the antibodies directly to the polymer, without this intermediate coupling. Monomer-modified antibodies and single stranded DNA are commercially available and can be directly copolymerized into a capture gel, but this modification is usually more expensive than the biomolecule itself. Therefore, it is preferred to perform these conjugation steps in-house. Several methods exist to create such functional polymers. Two pathways can be distinguished: co-polymerizing a functional group into the polymer that can react with an antibody post-polymerization, and modifying antibodies with a group that can be co-polymerized. The second approach is favorable in this situation, since the modified antibodies stay stable over time, while the reactive groups in the polymer might degrade during long-term storage. Proteins have multiple primary amine groups (N H2) on the surface due the common amino acid lysine and at N-terminus of the peptide chain. These primary amines are function groups that are most commonly being targeted for conjugation. Primary amines can form stable amide linkages by reacting them with activated esters. Among these activated esters, n-hydroxysucciminide (NHS) is the most commonly used. Activated ester monomers, a class of molecules that consist of both a polymerizable end group and an activated ester, can be used to modify an antibody in such a way that it can be co-polymerized. One such activated ester monomers is N-hydroxysucciminide acrylate (NSA), shown in FIG. 8, which consists of a NHS ester together with an acrylate group that can be co-polymerized in an acrylamide hydrogel due to its vinyl group. If NSA reacts with the amine group of a protein, it forms a stable amide bond between the protein and the acrylate.

NSA has been described for use to conjugate enzymes with monomers and subsequently immobilize enzymes by copolymerizing them with free monomers. When enzymes are incubated with NSA in a 1:10 molar ratio, on average one vinyl group will be conjugated to each enzyme while only 3% of the enzyme activity got lost per vinyl group added to the enzyme.

The polymerization can take place either inside or outside of the device. It has been demonstrated how a ssDNA modified monomers can be polymerized inside a device using UV light. UV polymerization using masks allows for good positional control of the hydrogels inside the device. However, the UV light might degrade the antibodies in the gel depending on the wavelength. Furthermore, the polymerization step needs to be repeated for every single step, which can be time consuming. Alternatively, a large batch of linearly polymerized antibody conjugated polyacrylamide, as shown in FIGS. 9A-9E, could be prepared up front and stored. Since this capture gel is linearly polymerized, and thus viscous, the hydrogel can still be injected into the device. A physical blockade in the microchannel can hold the hydrogel in place. After use, the hydrogel can be flushed out of the chip again and the chip can be reused.

In some implementations, antibodies are incubated with NSA in a 1:10 molar ratio overnight at 4 degrees Celsius in order to introduce a vinyl group to the antibody. 2 µM acrylamide modified antibody is added to a 4% acrylamide monomer solution without cross linker by adding ammonium persulfate and tetramethylethylenediamine and is linearly polymerized resulting in a viscous but injectable hydrogel.

Sample Injection

In order to detect the analyte, the sample must be transported through the capture region. This can be done by means of a pressure driven flow through the microchannel, induced using an external pump. However, external pumps are expensive and cannot be miniaturized and integrated into a chip and thus takes away some of the major advantages of microfluidics. Integrating micropumps inside microfluidic devices has been demonstrated, for example, consisting of multiple microvalves, but increases the complexity and cost of chips. Moreover, moving mechanical parts can compromise the re liability of the device. Another disadvantage is the parabolic flow profile that develops in a pressure driven flow, which leads to sample dispersion. This makes it impossible to transport an equal concentration of sample throughout the cross sectional area of the sensing region inside the biosensor. The regions near the walls of the microchannel will receive next to none of the sample due to the no-slip properties of the walls. Furthermore, if a functionalized hydrogel is used to capture the analyte in a 3D matrix, a pressure driven flow cannot be used as it will push the hydrogel out of the channel.

Electrokinetic Methods

Easier miniaturization and a more favor able flow profile can be obtained by relying on electrokinetically methods for fluid transport. In some implementations, electrokinetics is currently the preferred method for fluid actuation in microdevices. The underlying mechanisms behind electrokinetics are more complex than pressure driven flows, and a thorough understanding of these concepts is necessary to optimally benefit from the possibilities of electrokinetics. Electrokinetic fluid transport is based on two underlying mechanisms: Electroosmosis and electrophoresis. Electroosmosis is the bulk movement of liquid past an immobilized solid charged surf ace in the presence of an applied electric field. Electrophoresis refers to the movement of a charged mobile surface inside stationary bulk liquid under the application of an applied electric field. Electroosmosis thus causes a mass transfer of fluid, while electrophoresis induces movement of charged particles. Under certain assumptions, the flow velocity of both electroosmosis and electrophoresis can be described by the Helmholtz-Smoluchowski equation 2.1 below:

$$u = \frac{\varepsilon \zeta E_x}{\eta}$$

Where u is the induced fluid velocity in electroosmosis or particle velocity in electrophoresis, ε the permittivity of the solution [F/m], ζ the zeta-potential, or surface potential of either the charged fixed surface in case of electroosmosis, or the surface of the charged particles in case of electrophoresis [V], $E_x$ the applied electric field [V/m] and η the viscosity of the fluid [pa·s]. This velocity is independent of the cross-sectional position in contrary to a pressure driven flow if the electric field is applied along the channel. The fluid flow or particle velocity is constant throughout the cross-section of the channel, which is called plug flow. This flat flow profile is advantageous when the goal is to transport a fixed volume of sample through the sensing region of the micro-device.

Injection Schemes

Figure 10A:
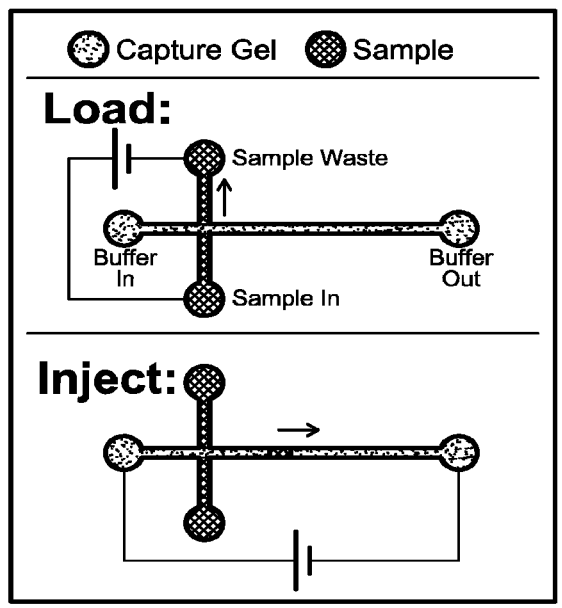
FIG. 10A illustrates a cross injection type of Electrokinetic injection.
Figure 10B:
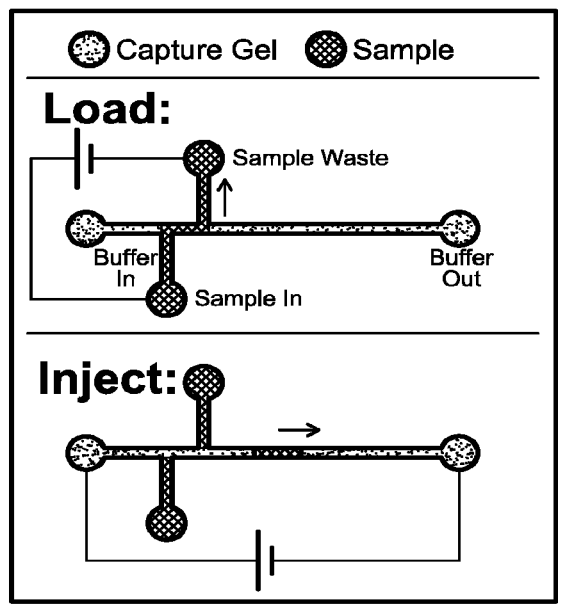
FIG. 10B illustrates a double-T injection type of Electrokinetic injection.

The injection of small, well-defined and repeatable amounts of sample into the sensor is a key step in the design of the microfluidic devices. The injection of such volumes using electrokinetic methods is called Electrokinetic injection and found its origin in microfluidic electrophoretic separation microchips. Several setups for electrokinetic injection have been reviewed and the most widely used design is the cross injection shown in FIG. 10A. This design consists of two orthogonal channels and based on the applied potentials, several injection modes can be performed with this design. FIGS. 10A and 10B show the floating mode, a basic injection scheme which consists of two steps: the sample is first loaded into the device due to an applied potential between the sample inlet and the sample waste while the other two reservoirs remain at floating potential, followed by the application of an electric field between the buffer inlet and buffer waste reservoir while the other two reservoirs remain at floating potential. The electric field causes electrokinetic transport of the charged molecules in the intersection between the two perpendicular channels.

One downside of the floating mode is diffusion that occurs during the loading step. Sample diffuses from the sample channel, indicated in red in FIGS. 10A and 10B into the perpendicular buffer/transport channel, indicated in blue. In order to prevent diffusion, more complex injection modes can be employed. According to Blas et al., the most widely employed injection mode for the cross injection is the pinched mode. In pinched mode, the potential of the buffer-in and buffer-out reservoirs is kept at a value somewhere between the sample-in and sample-waste reservoir potentials. This way, during the loading step, buffer solution flows from both sides of the device towards the sample waste reservoir, which pushes the diffusing sample back and thus prevents diffusion during the loading step. In pinched mode, the potential in all reservoirs must be controlled in each step of the injection process. As the amount of reservoirs and channels increase, it becomes a complex task to balance all potentials on each reservoir to create the desired transport in each channel. Kirchhoff's rules for a resistive network can be used to model the transport in an electrokinetically driven microsystem. Every channel can be seen as an electrical resistor, and the potentials in the reservoirs as voltage sources. The resulting current over each resistor gives an accurate prediction for the flow of charged species trough each channel.

Although the cross injection setup is capable of injecting small, repeatable amounts of liquid, the injected sample volume is limited by its geometry; the channel dimensions at the inter-section between the two perpendicular channels determine the injected sample volume. For electrophoretic separative microsystems it is indeed favorable to have narrow bands with a small volume in order to get a high separation efficiency. However, for the purpose of sensing, higher volumes per injection might be favorable. The volume of an injection can be increase by using a so-called double-T injection. This design is shown in FIG. 10B. By spacing the two side-channels further apart, the injected volume can be increased.

Impedance Spectroscopy Theory

A sample can be electrokinetically transported across the sensing region, where the analyte will bind to the immobilized antibody inside the capture gel. We aim at using impedance measurements to detect binding in order to test the hypothesis whether this setup will decouple sensitivity and dynamic range. Bound proteins block the current path, which causes a change in electrical properties of the gel, as already discussed in previous sections. If we neglect the capacitive behavior of proteins, the sensor is basically a microfluidic conductivity sensor that measures the electrical resistance of the capture gel. Electrical resistance is defined by Ohm's law as the relationship between electrical current and potential, given by equation 2.2:

$$R = \frac{U}{i}$$

Figure 11A:
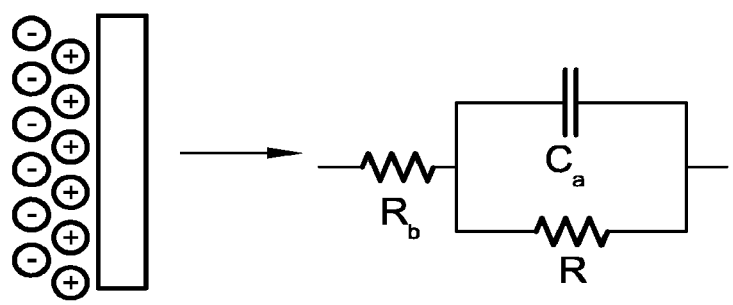
FIG. 11A is an illustration of the EDL formed at the electrode-electrolyte interface and a corresponding equivalent circuit to model this interface, consisting of the bulk resistance $R_b$, the double layer capacity $C_{dl}$ and the double layer resistance R.
Figure 11B:
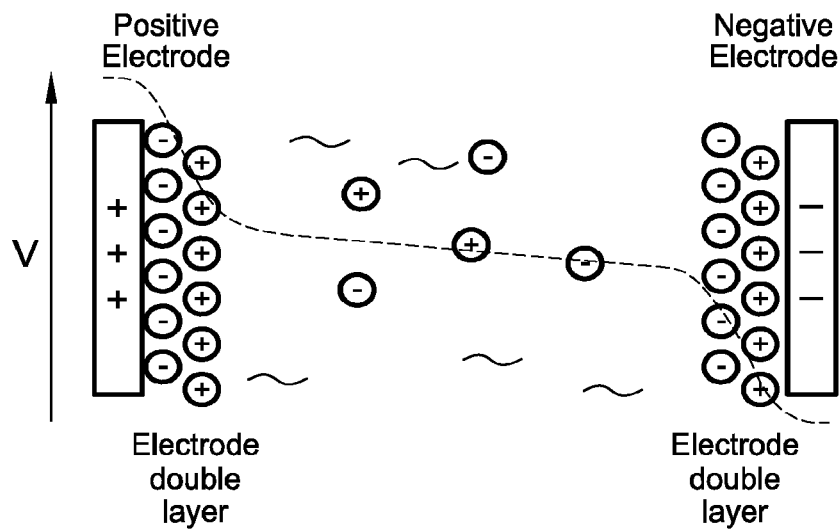
FIG. 11B is an illustration of a measurement with two electrodes immersed in an electrolyte, indicating the formation of a double layer, and a significant voltage drop over the EDL.

Here, R [Ω] is the electrical resistance, U [V] is the voltage measured across the resistor and i [A] is the current flowing through the resistor. If the resistance is the parameter of interest, in a simple electrical circuit, one can apply a voltage over this resistor and measure the current to obtain the unknown resistance. However, Ohm's law only holds in case of an ideal resistor, which has a linear relation between voltage and current over an infinite range and where the resistance is independent of the frequency. These assumptions do not hold for measurements in electrolytes. When electrodes are in contact with an electrolyte and a potential is applied across they will attract ions of the opposite charge and a charged layer starts to form near the interface. This layer is called the electrical double layer (EDL). The EDL introduces a capacitance, called the double layer capacitance, and a certain charge transfer resistance. In absence of Faradaic currents, i.e., no reduction or oxidation reactions happening at the interface, the EDL can be modeled as a parallel capacitor and resistor, as shown in FIG. 11A. The impedance of a capacitor is inversely related to the frequency. Therefore, in DC or at low frequency AC measurements, the double layer will introduce a high impedance, resulting in a large potential drop over the electrode-electrolyte interface and a near absence of electric field in the solution, as indicated in FIG. 11B. In electrochemical impedance spectroscopy, a small sinusoidal voltage is applied between two electrodes, and the resulting current is measured. The relationship between the voltage and current is called impedance, a complex quantity. The magnitude of the impedance gives the relationship between the amplitude of the current and the amplitude of the voltage, as in Ohm's law, while the argument describes the phase difference between the applied potential oscillation and the measured current oscillation. Since the perturbation voltage is usually small, the voltage-current response has a linear behavior. In electrochemical impedance spectroscopy, impedance is measured over a range of frequencies to obtain information about the capacitive and resistive properties of the sample and of the electrode-electrolyte interfaces.

Electrode Design

Figure 12:
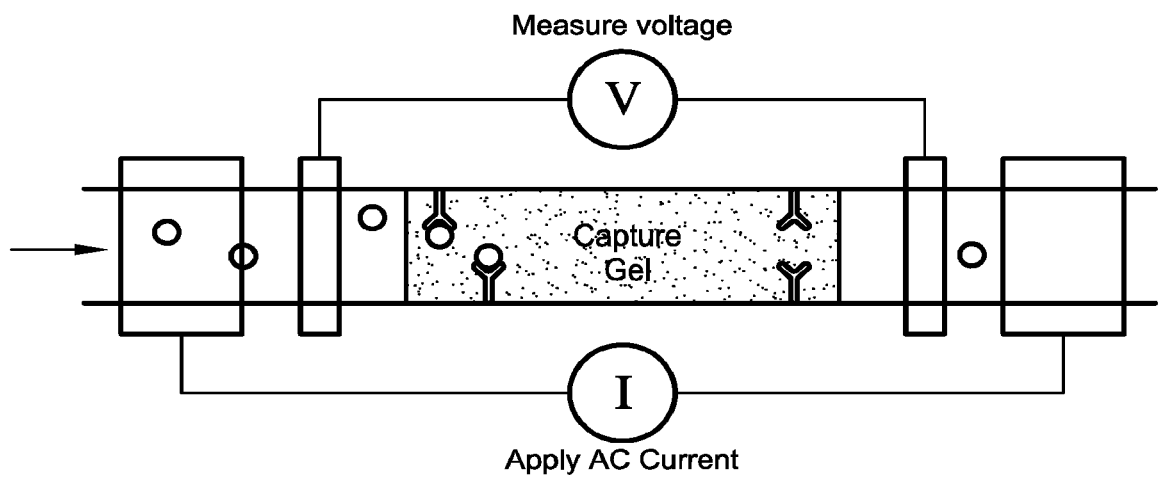
FIG. 12 illustrates a four electrode setup integrated in a microfluidic channel measuring impedance of a capture gel.

When the impedance of the capture gel is the parameter of interest, it is desirable to filter out the impedance due to the electrode-electrolyte interface. A possible approach is a differential approach, where one measures the impedance before starting the experiment, which is subsequently subtracted from actual measurements. However, the confidence of this approach is questionable if the double layer impedance becomes several orders of magnitude larger than the parameter of interest, which is likely at low frequencies. A four-electrode measurement setup is one where a current is applied trough the sample using two outer electrodes while the voltage is measured between two inner electrodes. This setup, in its most straight forward design in a microfluidic channel is shown in FIG. 12. If the inner 'pickup' electrodes are placed sufficiently far away from the electrodes that generate the current, the potential drop over the double layer is not observed and only the impedance of the capture gel is effectively measured.

Sensor Design

A two-layer microfluidic device was designed using SOLIDWORKS, consisting of a layer of microfluidics and a layer of electronics. The microfluidic layer is a thermoplastic, hot-embossed chip that defines the microchannels in the device responsible for electrokinetically injecting well-defined volumes of sample into the device. The layer of electrodes is in contact with the microchannel in order to perform impedance spectroscopy.

Microfluidics

Figure 13:
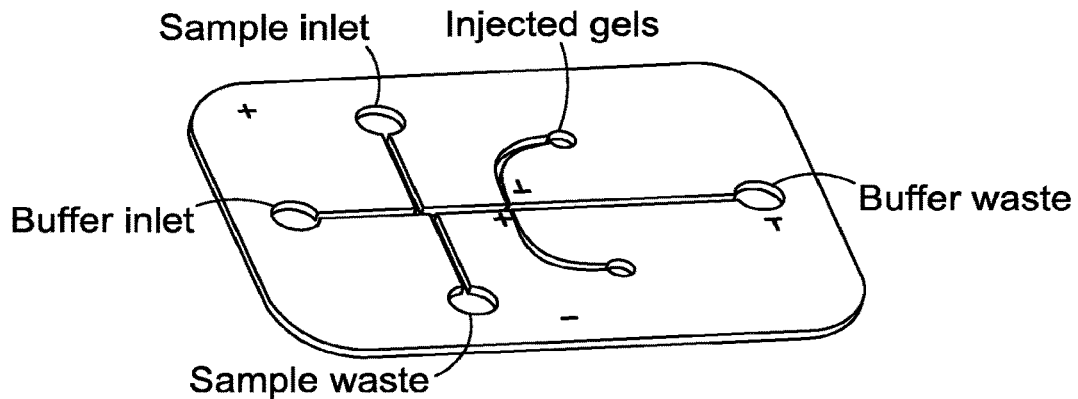
FIG. 13 illustrates a schematic design of a microfluidics layer.

Referring to FIG. 13, the microfluidic layer consists of a microchannel (e.g., main channel of the microfluidic layer) over the length of a chip, with two perpendicular side channels that function as a double-T injection, and two additional side channels that help positioning hydrogels inside the device which is discussed later. Channel width and height are uniform for all channels in the chip. For the purpose of studying the relationship between the channel geometry and sensitivity, chips with four different channel geometries were designed with channel dimensions (width, height, in μm) of 50 by 50, 50 by 100, 100 by 50 and 100 by 100. For the purpose of manufacturing these 4 microfluidic parts by hot embossing in thermoplastics, a mold was designed.

According to some implementations, microfluidics with an electrokinetic injection system is used to inject constant, quantified samples inside the hydrogel using electrophoresis. Microfluidics can be fabricated by hot embossing the chips out of cyclic olefin polymer (i.e., COP).

Electrodes

Figure 14:
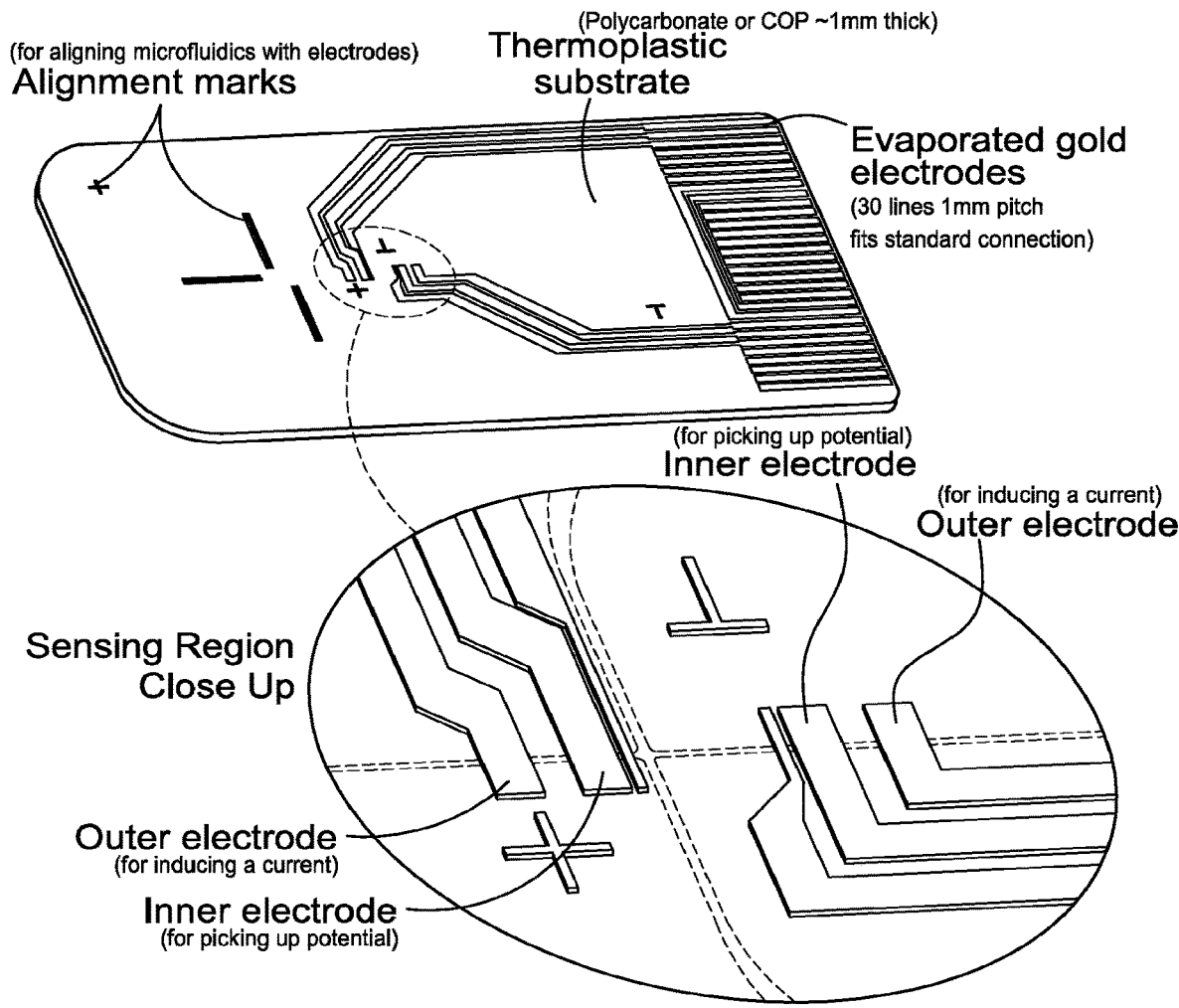
FIG. 14 illustrates a schematic design of an electrode layer.

Electrodes were designed to fit a 30 pin 1 mm pitch edge mount connector for easy interfacing with measurement equipment. Not all connections are utilized, but this leaves possibilities for future redesigns. Alignment marks are included in the electrodes to facilitate alignment of the electrodes with the microfluidics. The electrode layout, including dimensions, is shown in FIG. 14. Three devices could be manufactured on a single wafer.

Because the capturing (e.g., of the analyte of interest) does not occur on the surface of the electrodes, the electrodes can be decoupled from the capture site (e.g., the portion of the main channel including the capture hydrogel that bonds with the analyte of interest). This means that the dimensions of the electrodes are not constrained to the dimensions of 3D matrix. In some implementations, the electrodes can be made relatively larger independent of the 3D matrix in order to reduce noise, and the dimensions of the capture region (e.g., length of capture gel, width of capture gel, height of capture gel, etc.) can be designed to meet the goals of the assay and not subject to detection electrode design considerations. As shown in FIG. 14, planar electrodes are used, which care relatively easy to manufacture and only one layer of electrodes is required, although the electrodes can be positioned in any number of layers (e.g., 1, 2, 3, 5, etc.).

Two electrodes are placed on either side of the gel. A small alternating current is applied between two outer electrodes and a drop in potential is measured between the two inner electrodes. The drop in potential is representative of the resistance and capacitance of the capture gel. Binding of biomolecules into the gel will affect both resistive and capacitive responses.

Device Fabrication

FIGS. 15A-15C show an overview of the techniques used to fabricate the devices.

The molds were machined in aluminum using a Microsolution 5100-S micromilling platform (Microsolution, USA) with a resolution of 1 micron. This mold was used to emboss polycarbonate (PC, Bayer, Germany) and Cyclo Olefin Polymer (COP, ZEON, Japan) sheets to obtain microfluidic chips using a WABASH PS3H-8-CLX vacuum hot press (WABASH, USA), as shown in FIG. 15A. This process was performed between two glass plates which were thoroughly cleaned by sonicating before use for optical flatness. Microfluidic COP chips were hot embossed at 170-C and 27 K N (3 US Tons) using this mold. Through-holes were drilled using a drill press. These microfluidic chips were subsequently washed with soap, rinsed, sonicated in IPA, dried under nitrogen flow and corona treated to activate the surface prior to bonding.

Electrodes were kindly fabricated by a coworker (William Leineweber) on 1 mm PC substrates and 100 μm COP film. PC and COP were cleaned with oxygen plasma (20 sccm, 100 W, 2 minutes). 10 nm titanium and 100 nm gold were deposited via E-beam Evaporation (Denton Vacuum, USA) at 10-7 Ton. Shipley 1805 Positive Photoresist (Dow Chemical Company, USA) was subsequently spin coated on these substrates at 4000 rpm for 45 seconds. This photoresist layer was patterned using a Suss MJB4 mask aligner (SUSS MicroTec AG, Germany) with a UV exposure of 50 mJ/cm$^2$, then subsequently developed in CD-26 for 70 seconds, rinsed with water, and dried with compressed N2. The metals were wet etched with acid. The gold was etched with a standard Gold Etchant, and the Ti was etched with 7:1 Buffered Oxide Etch. Finally, the remaining layer of photoresist was removed by sonicating the electrodes in IPA.

Several methods were explored for bonding the microfluidics and electrodes including thermal bonding under pressure and solvent assisted laminating. For COP, solvent assisted bonding was performed using o-xylene (Sigma Aldrich, USA), diluted 1:1 in IPA. Xylene solution was pipetted onto the electrodes and the flat outer surfaces of the feature side of the microfluidics, avoiding contact between the solvent and the microchannels. Excess solvent was dried under nitrogen flow and the two parts were aligned under the microscope. 10 μl 10% o-xylene in IPA was carefully wicked in between the two parts by means of capillary action to prevent the two layers from misaligning. The aligned chip was either laminated at 137° C. or bonded in the hot press at 115° C./3.75 M P a between a glass plate and a 3 mm piece of silicone to distribute force uniformly during the bonding.

Hydrogel Chemistry—Conjugating Antibodies with a Vinyl Sidegroup

The final hydrogel is based on a tris(hydroxymethyl) aminomethane—glycine (TG) buffer solution. However, primary amine groups in both tris and glycine will interact with the reactive ester in N-hydroxysuccinimide acrylate (NSA), which will decrease the conjugation efficiency of vinyl groups to the antibodies. Therefore, the incubation of antibodies with NSA was per-formed in a phosphate-buffered saline (PBS) solution (Gibco, USA). NSA (TCI Chemicals, Japan) was dissolved in a 1×PBS buffer solution with pH of 7.5. 100 µl of 2 mg/ml anti-bodies for bovine serum albumin (anti-BSA, polyclonal from rabbit, ThermoFisher Scientific, USA) were mixed with 100 µl of NSA solution in PBS in order to create a 1:10 molar ratio of anti-BSA to NSA. This ratio has been shown to introduce on average one vinyl sidegroup to L-asparaginase, and the same protocol was used for anti-BSA without any further characterization or optimization. The mixture was briefly shaken and stored in a fridge at 4° C. overnight to prevent the antibodies from degrading. No washing or separation steps were performed afterwards.

Polymerization

TG buffer (Amresco, USA) was obtained as 10× solution and diluted to 1× in DI water. 40% Acrylamide solution without cross-linking agent (Sigma-Aldrich, US) was mixed with tris-glycine buffer to create several samples with a concentration ranging between 2% and 5% acrylamide. Acrylamide solutions were sparged for 5 minutes with argon to remove all oxygen from the solution, which would react with the free radical and inhibit the polymerization. A combination of ammonium persulfate (APS, Sigma-Aldrich, USA) and tetramethylethylenediamine (TEMED, Sigma-Aldrich, USA) which functioned as a free radical polymerization initiator. Titrations of the concentration of initiators were performed to find optimal polymerization conditions, which was visually determined by inspecting the viscosity of the polymer gels. The optimal concentration of initiators was the concentration that led to the highest viscosity, as this would indicate the longest polymer chain length. The optimum concentration was found to be 0.5 mM equimolar concentration of APS and TEMED for a gel without antibodies. This gel is referred to as transport gel.

After optimizing the polymerization process, 2 µM vinyl-modified anti-BSA was added to solutions of 3% acrylamide monomer solution to copolymerize the antibodies in a 3D matrix. After sparging, 1 mM of APS and TEMED was added to this solution to initiate the polymerization, a concentration slightly higher than found in B.3, which resulted in higher viscosity gels in presence of the antibody solution. The solutions were stored at 4° C. overnight to finish the reaction. After inspection of the viscosity, 10 µM 1 mg/ml cascade blue was added to the gel, gently mixed on a vortex shaker preventing bubbles to form and stored at 4° C. to prevent the proteins from degrading. This gel is referred to as capture gel.

Fluid Handling

Additional manifolds were developed for fluid handling, one for injecting hydrogels and one for positioning electrodes for electrokinetic injection. These manifolds were designed in SOLID-WORKS and laser cut in acrylic in a specific shape to fit on top of a microscope stage.

Hydrogel Positioning

It is important to position the capture gel between the two pickup electrodes in order to measure a change in impedance upon binding of proteins to the capture gel. For this purpose, two channels are present inside the sensor. The injection scheme is shown in FIG. 16A. First, the chip is plasma treated in a Diener ATTO low pressure plasma chamber (Diener, Germany) to make the inner channel walls hydrophilic. Next, the chip is placed in the hydrogel injection manifold in and the screws are tightened to create a watertight connection between the manifold and the chip, and connected to syringes as shown in FIG. 16B. Next, the entire chip and all tubing is filled with TG buffer, to prevent air bubbles entering the channels. Two 1 ml syringes are filled with gels that were degassed under vacuum prior to use, one with the transport gel (e.g., plain gel without antibodies/receptors) and one with the capture gel, mixed with cascade blue. The syringe with the transport gel is connected to inlet C, as shown in, for example, FIG. 7A, and fills the entire chip with hydrogel. Next, inlets A, B and F are closed and the capture gel is injected from inlet D to inlet E, while applying a small pressure on the syringe at inlet C to prevent capture gel moving out of the detection area. This is performed on a Zeiss axio observer epifluorescence microscope (Zeiss, Germany) to accurately monitor the flow of functionalized hydrogel inside the chip.

As shown in FIG. 16A an intersection is present in the fluidic channel to create a sharp cutoff while injecting the functionalized gel. In some implementations, the chip is initially filled with a plain gel without antibodies from inlet C. While applying pressure on inlet C, the functionalized gel is injected from inlet D making it deflect. Finally, the plain gel is injected from inlet C without applying pressure on inlet D in order to create a sharp interface between the two gels.

Calibration Curve

Protein capture validation and characterization was performed using the epifluorescence microscope with a 10× objective at 100% LED intensity. For this purpose, BSA was labeled with Alexa Fluor 488 such that captured BSA will return a fluorescent signal. Although this is sufficient to qualitatively validate the binding, it does not provide quantitative information on the amount of captured protein. This requires a calibration curve which links the fluorescent intensity to the concentration of bound protein. Data points for this curve were obtained by injecting PBS solution with known concentrations, c, of BSA in the chip. The fluorescence intensity inside a microfluidic channel, I, for each BSA solution was observed under the microscope and measured at exposure times of 100 ms, 250 ms, 500 ms, 1000 ms and 1500 ms. For each of these exposure times, a logistic function, given in equation 3.1, was fitted through the obtained concentration-intensity data. Parameters a, b and $I_{max}$ were fitted with a least squares method. The equation of the curve was subsequently formulated into equation 3.2 to estimate the concentration c of BSA inside a region within the chip.

$$I(c) = \frac{I_{max}}{1 + e^{-a(c-b)}} \quad \text{Equation 3.1}$$

$$c(I) = -\frac{1}{a}\ln\left(\frac{I_{max}}{I} - 1\right) + b \quad \text{Equation 3.2}$$

Electrokinetic Injection—Reservoir Potentials

Figure 17:
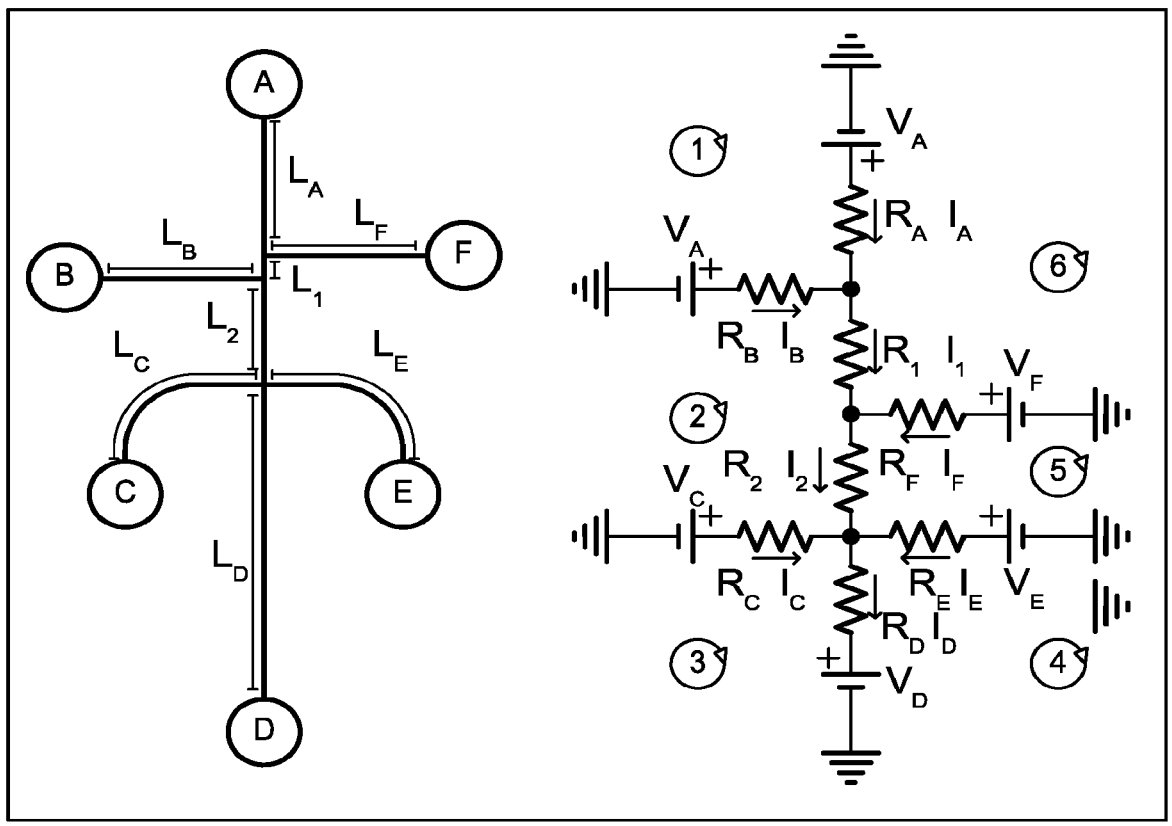
FIG. 17 illustrates microfluidic channels and an equivalent circuit used to calculate reservoir potentials.

Electrokinetic fluid transport is driven by an electrical field over the microchannels. This field is applied by suspending 6 platinum wires in the wells of the microfluidic chip. An acrylic manifold holds these electrodes in place while a LabSmith HVS448 programmable voltage source (LabSmith, USA) controls the voltage in each well. Two steps are programmed in the voltage source for loading and injection. The six reservoirs are labeled A-F and the eight channel segments are named accordingly, as shown in FIG. 17. The length of each channel segment is indicated with Lx. Potentials in each well are determined. In case the channel geometry is uniform throughout the chip, the electrical resistance of each channel segment is proportional to its length. Under this assumption, the microfluidic network can be described as an electrical circuit where each resistor represents a channel segment and where the applied potential in each reservoir is represented by a power source, as shown in FIG. 17. The resulting current is consequently proportional to the migration velocity of the charged species in the sample during electrophoresis.

The resulting electrical circuit can be solved using Kirchhoff's circuit laws. On each of the three nodes, Kirchhoff's first law states that the sum of the currents $i_k$ is zero.

$$\sum_{k=1}^{n} i_k = 0 \qquad \text{Equation 3.3}$$

Kirchhoff's second law states that the summation of the potential difference across the elements in the six loops indicated in FIG. 17 is zero:

$$\sum_{k=1}^{n} V_k = 0 \qquad \text{Equation 3.4}$$

The resulting nine equations, three for the nodes and six for the loops, form a linear system of equations given in equation (3.5)

$$\begin{bmatrix} -1 & 0 & 0 & 0 & 1 & 1 & 0 & 0 \\ 1 & -1 & 0 & 0 & 0 & 0 & 1 & 0 \\ 0 & 1 & -1 & 1 & 0 & 0 & 0 & 1 \\ 0 & 0 & 0 & 0 & R_B & -R_A & 0 & 0 \\ -R_1 & -R_2 & 0 & R_C & -R_B & 0 & 0 & 0 \\ 0 & 0 & -R_D & -R_C & 0 & 0 & 0 & 0 \\ 0 & -R_2 & 0 & 0 & 0 & 0 & -R_F & R_E \\ 0 & 0 & -R_D & 0 & 0 & 0 & 0 & -R_E \\ -R_1 & 0 & 0 & 0 & 0 & -R_A & R_F & 0 \end{bmatrix} \begin{bmatrix} i_1 \\ i_2 \\ i_D \\ i_C \\ i_B \\ i_A \\ i_F \\ i_E \end{bmatrix} = \begin{bmatrix} 0 \\ 0 \\ 0 \\ V_B - V_A \\ V_C - V_B \\ V_D - V_C \\ V_E - V_F \\ V_D - V_E \\ V_F - V_A \end{bmatrix} \qquad \text{Equation 3.5}$$

The length of all channels, and thus the electrical resistances are known and given in table 3.1. Under the assumption that the electrical resistance is proportional to the channel length, this system gives a direct relationship between the applied voltages in each reservoir and the resulting currents in each channel segment. A MATLAB script was written to determine the reservoir potentials. Potentials were chosen in such a way that during loading, $i_A$ is slightly positive and $I_1$ is slightly negative to create a pinched injection to prevent sample dilution during loading. During injection, potentials were chosen in such a way that $i_B$ and $i_F$ are slightly negative such that no sample leaks during the injection step, and $i_C$ and $i_E$ were chosen to be slightly positive in order to prevent sample from avoiding the capture gel by entering the sidechannels.

TABLE 3.1

| Length of each channel segment in mm | | | | | | | |
|---|---|---|---|---|---|---|---|
| $L_A$ | $L_B$ | $L_C$ | $L_D$ | $L_E$ | $L_F$ | $L_1$ | $L_2$ |
| 6.5 | 1 | 5 | 7 | 7 | 14.5 | 9 | 9 |

Injected Mass

Figure 18:
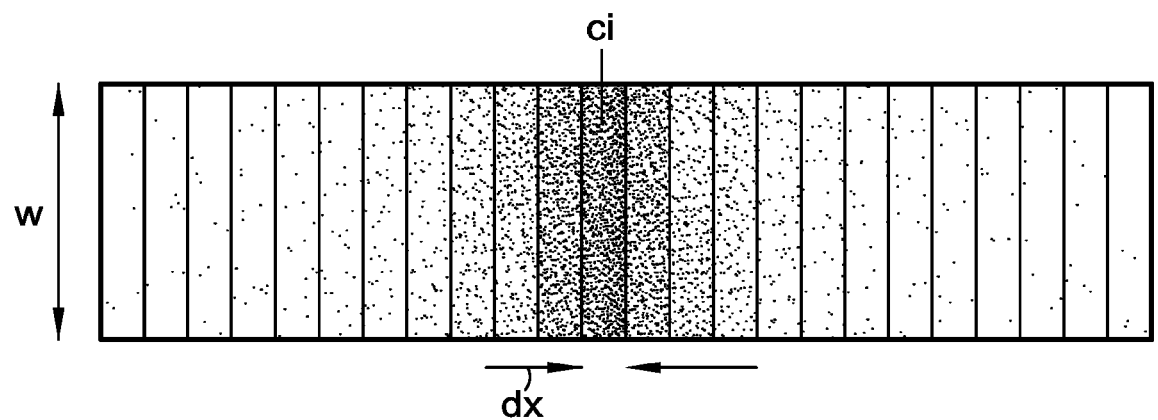
FIG. 18 illustrates a discretized volumes and associated concentrations ci.

During each injection, a certain amount of protein is being injected into the device. An intensity profile can be measured over the length of an injected plug. This intensity can consequently be correlated to a protein concentration called ci, by using the calibration curve discussed herein. This is illustrated in FIG. 18. The channel can be subdivided into n elements with each a concentration ci. The volume of each element is given by:

$$dv = hwdx \qquad \text{(Equation 3.6)}$$

Where w is the width of the channel, h the height of the channel and dx the width of an element, which is determined by the size of a single pixel. Under the assumption that the concentration is uniform over the width and height of the channel, the mass of protein in a single element is:

$$m_i = c_i hwdx \qquad \text{(Equation 3.7)}$$

The total mass of protein in the plug, $m_{plug}$ can be obtained by summing the mass over all n elements:

$$m_{plug} = \sum_{i=1}^{n} m_i = hwdx \sum_{i=1}^{n} c_i \qquad \text{(Equation 3.8)}$$

Protein Capturing

Protein binding to the capture gel was demonstrated and characterized by electrokinetically injecting samples of fluorescent labeled BSA into the anti-BSA capture gel. To save the electrodes, this process was tested in a chip without integrated electrodes. After the capture gel was positioned inside the device as described herein, the reservoirs, shown in the FIGS., were installed on the electrode and filled with 50 µl 1×TG buffer. The cascade blue was washed out of the channels by applying a voltage of 300 V on reservoirs C, D and E, while grounding reservoir A for 2 minutes. After this, the solutions in all six reservoirs were washed and replaced with new 1×TG buffer three times, to ensure all cascade blue was removed from the chip. Reservoir F was subsequently filled with 0.2 µM of fluorescent labeled BSA in 1×TG buffer. Samples were electrokinetically loaded into the double-T injector for about 1 minute and injected for another minute, both at 200 V/cm. The capturing was observed on the epifluorescence inverted microscope. This process was repeated several times to observe and characterize how the sample is being captured.

Impedance Measurements—Impedance Setup

Figure 19A:
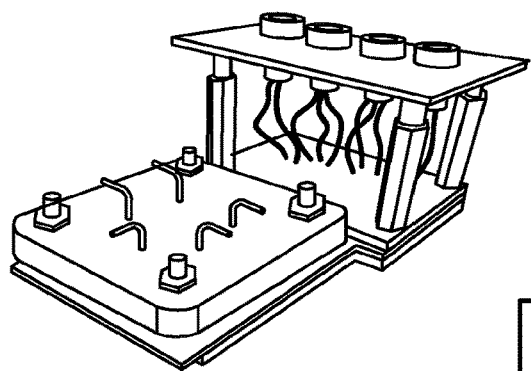
FIG. 19A illustrates a chip positioned inside a connector to interface with an impedance analyzer and a gel injection manifold connected to microfluidic channels in a setup that fits on top of a microscope.

The electrode layer was designed in such a way that it would fit a 30 pin edge connector. A PCB that connects the contacts of this connector to banana jack connectors was mounted on an acrylic laser-cut setup shown in FIG. 19A. This setup was designed to be mounted on the microscope while connected to the programmable power source trough the platinum wire manifold, shown in the FIGS., as well as to a potentiostat/galvanostat impedance analyzer. Impedance measurements were performed on an Autolab PGSTAT128N (Metrohm Autolab, the Netherlands) installed with the FRA32M impedance analysis module. Four terminal measurements were performed in a galvanostatic mode using an excitation current of 10 µA. To test this setup, 5 concentrations of TG buffer (0.5×, 1×, 2.5×, 5×, 10×) where injected in the chip and the corresponding impedance was measured.

Integration

Figure 19B:
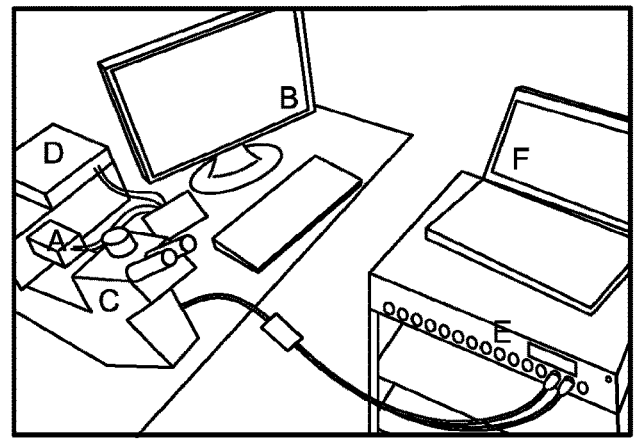
FIG. 19B illustrates a setup for performing protein capturing and impedance measurements simultaneously, where the setup includes a chip inside a connector setup with a jig of platinum wires suspended into a reservoir of the microfluidic chip, a computer for imaging and power control, an inverted fluorescent microscope, a programmable voltage source, an impedance analyzer, and a laptop to read out impedance measurements.

The setup for performing the experiments to determine the change in impedance upon capturing is shown in FIG. 19B. A capture gel was positioned inside a bonded chip with integrated electrodes as described herein, the cascade blue was washed out of the capture gel as described herein. The chip was inserted in the setup shown in FIG. 19A, reservoirs were installed and filled with 50 µl TG buffer and this setup was positioned on top of the epifluorescent inverted microscope. Reservoir F was filled with 50 µl of 0.2 µM Alexa Fluor 488 labeled BSA. The platinum wires were suspended into the reservoirs and connected to the power source. The impedance analyzer was connected to the setup on the microscope. Samples were electrokinetically injected in the chip as described herein. One computer was used to control the power source while observing the movement and capturing of fluorescent labeled BSA, while another computer was used to perform impedance measurements. Care was taken to remove the connectors from the impedance analyzer during electrophoresis, as the high voltages during electrophoresis might damage the impedance analyzer, which is not suited for such high voltages.

The development of the sensor is split into several subtopics: Chip fabrication, Hydrogel positioning and calibration, electrokinetic injections, protein capturing and impedance spectroscopy. First, the chip fabrication process was optimized, and chips were fabricated to validate the individual subtopics. The electrokinetic injection was tested inside a microfluidic chip, the protein capturing was tested inside a microfluidic chip, and the impedance spectroscopy was tested inside a microfluidic chip with integrated electrodes. Finally, after each component was tested and validated, all components were integrated together.

Chip Fabrication—Microfluidics and Electrodes

Figure 20A:
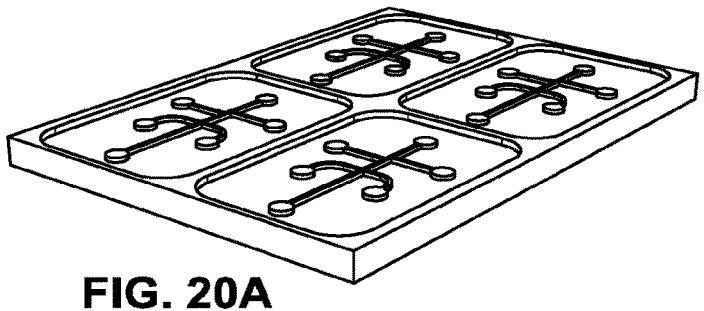
FIG. 20A illustrates an aluminum mold used for hot embossing.
Figure 20B:
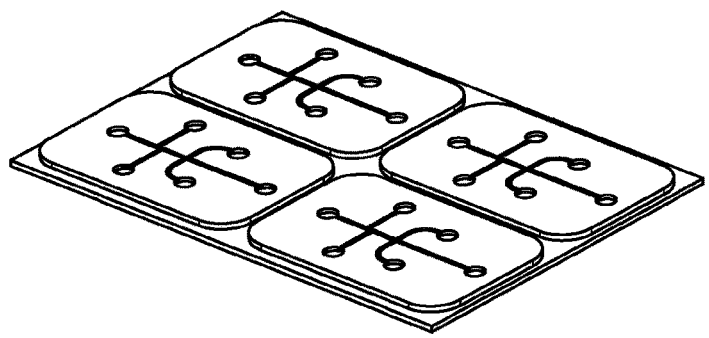
FIG. 20B illustrates the resulting COP thermoplastic part after the embossing of FIG. 20A, which includes four microfluidic chips with varying channel dimensions.
Figure 20C:
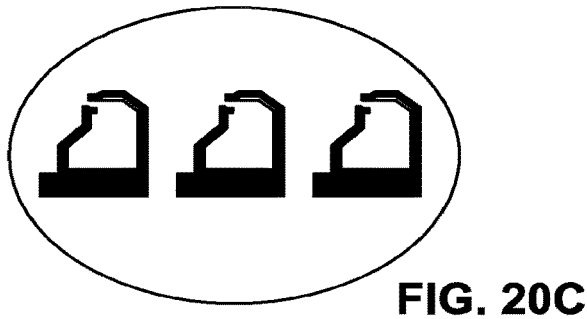
FIG. 20C illustrates gold electrodes on a COP wafer.

FIG. 20A shows the milled aluminum mold containing four chip designs. This mold was used to hot emboss the thermoplastic chips shown in FIG. 20B. Best results for hot embossing COP was obtained at 170° C. at 2722 kg (3 US tons) for 15 minutes. COP hot embosses faster and at lower temperatures than polycarbonate due to its lower glass transition temperature. Also, features in COP chips were better defined than in polycarbonate chips, as less air bubbles were present after embossing. FIG. 20C shows a wafer with 3 electrodes on COP after etching. Electrodes on COP were fabricated and showed good adhesion between the substrate and the metal, as evidenced by the tape test.

Bonding

Figure 21:
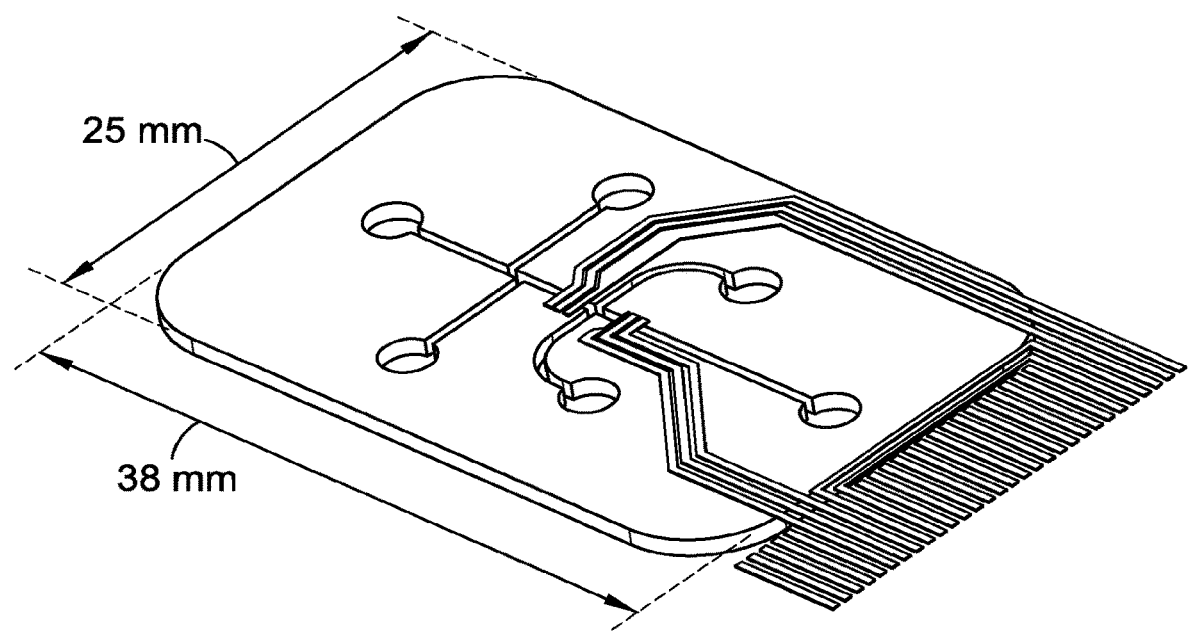
FIG. 21 illustrates a bonded chip.

A wide range of conditions for solvent assisted thermal bonding were explored, using both hot-press bonding and lamination. The preferred bonding method was chosen to be laminating COP chips because of the rapidity of the process and compatibility with large scale manufacturing. Optimal bonding conditions for lamination were obtained at 137 degrees Celsius after the microfluidics were exposed to a 1:1 solution of Xylene and IPA for 60 seconds, and the electrodes for 120 seconds. This bonding method resulted in little deformation of the channels and alignment marks, good transparency and no physical damage of the electrodes. FIG. 21 shows a bonded chip after this procedure.

Hydrogel Positioning

Figure 22:
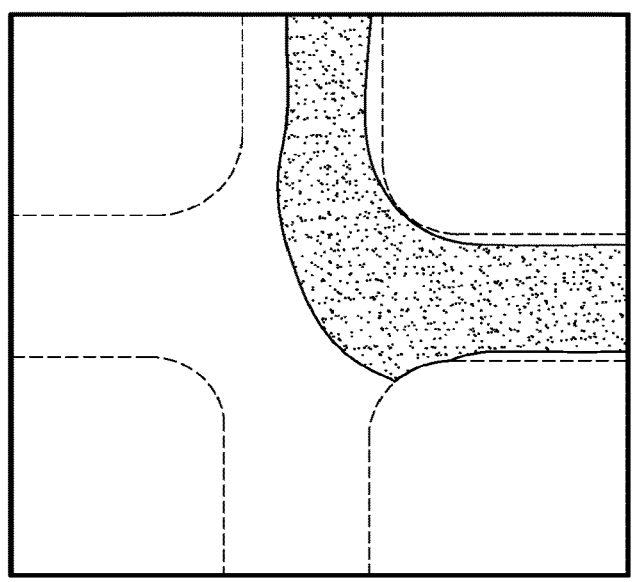
FIG. 22 illustrates a close up view of an intersection after positioning capture gel, wherein a bright intensity indicates a fluorescent signal of cascade blue mixed with the capture gel.

FIG. 22 shows the position of the capture gel, indicated by the lighter color, after injecting the two gels. The capture gel, mixed with cascade blue, shows a relatively sharp interface with the transport gel in the intersection between the two channels. The interface is not symmetric, but this is not expected to cause any significant problems since the flow of proteins will be slightly focused in the cross due to electrophoretic pinching from the gel injection channels during the injection step. After positioning the gels, care should be taken in removing the gel injection manifold. Releasing the pressure on the gaskets causes a slight suction which can alter the position of the interface. Cascade blue slightly overlaps with Alexa Fluor 488 in emission spectra, at a wavelength of around 500 nm and should therefore be removed before capturing proteins. Since cascade blue is a negatively charged dye, it could easily be washed out to the buffer waste sample by applying a positive potential at reservoir D and grounding reservoir A, while the covalently bound antibodies will remain in place.

Calibration Curve

Figure 23:
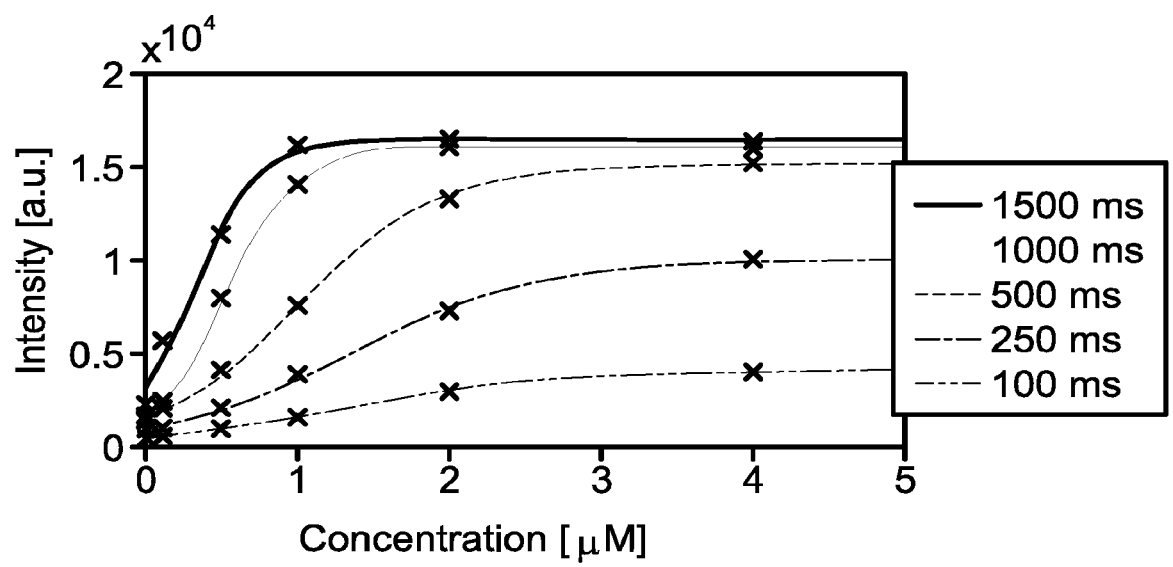
FIG. 23 illustrates a calibration curve of Alexa Fluor 488 labeled bovine serum albumin, where the sensor intensity output is in the range between 0 and 16431 units, and each line indicates a logistic fit through the measured intensity in a channel for each concentration of protein, at varying exposure times between 100 ms and 1500 ms.

FIG. 23 shows the intensity of Alexa Fluor 488 labeled BSA for exposure times of 100, 250, 500, 1000 and 1500 ms, and a logistic function from equation (3.1) fitted through the data. As can be seen, the curves for 500, 1000 and 1500 ms plateau at the saturation intensity of the sensor, which was 16431 units. Curves at 100 and 250 ms did not show this plateau. The corresponding fit parameters a, b and $I_{max}$ for the logistic function are shown in table 4.1.

Exposure times of 1000 and 15000 ms would be most suitable to measure concentrations below 1 µM. Exposure time of 500 ms would be most suitable for concentrations between 0.5 and 1.5 µM while an exposure time of 250 ms would be most suitable around 2 µM. This collection of calibration curves allows the performing of experiments over a varying range of protein concentrations while still being able to quantify the data.

TABLE 4.1

Fit parameters a, b and $I_{max}$ for the logistic function of equation 3.1 through the intensity-concentration data measured in a microchannel for exposure times between 100 and 1500 ms, shown in FIG. 23.

| Exposure time [ms] | A | b | $I_{max}$ |
|---|---|---|---|
| 100 | 1.36 | 1.29 | 41831 |
| 250 | 1.64 | 1.34 | 10054 |
| 500 | 2.15 | 1.0 | 15153 |
| 1000 | 4.16 | 0.51 | 16108 |
| 1500 | 4.65 | 0.30 | 16431 |

TABLE 4.2

Theoretically estimated potentials (in V) for the electrokinetic injection used as initial values and experimentally optimized potentials (in V) after tweaking the pinching and pullback during loading and dispensing A-F indicate reservoirs (see FIG. 17).

| | Loading | | Injecting | |
|---|---|---|---|---|
| | Calculated | Experimental | Calculated | Experimental |
| A | 130 | 110 | 0 | 0 |
| B | 350 | 350 | 50 | 42.5 |
| C | 100 | 110 | 55 | 20 |
| D | 50 | 0 | 150 | 150 |
| E | 100 | 110 | 55 | 20 |
| F | 0 | 0 | 45 | 37.5 |

Electrokinetic Injection—Reservoir Potentials

Figure 24A:
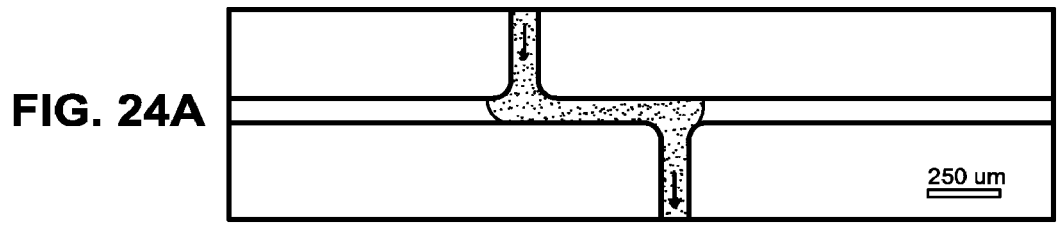
FIG. 24A illustrates a loading step of the electrokinetic injection process in a floating mode where a sample diffuses into a loading channel.
Figure 24B:
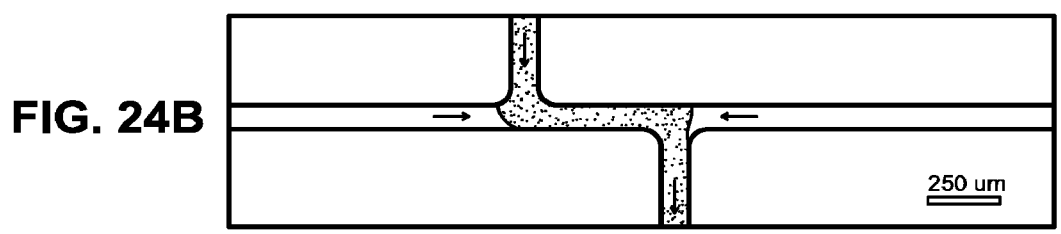
FIG. 24B illustrates the loading step during a pinched injection, pre-venting diffusion, of the electrokinetic injection process of FIG. 24A.
Figure 24C:
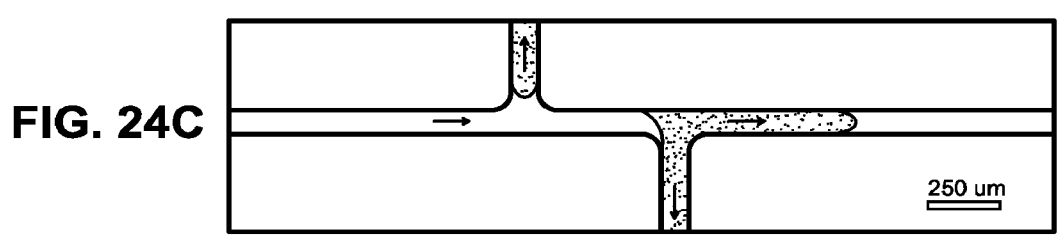
FIG. 24C illustrates an initiation of the injection of the electrokinetic injection process of FIG. 24A.
Figure 24D:
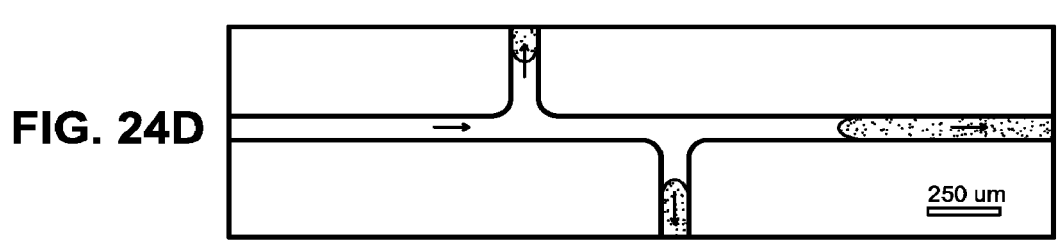
FIG. 24D illustrates a sample exiting the double-T injector of the electrokinetic injection process of FIG. 24A while the sample is being pulled back in the loading channel, where the width and depth of all channels is 100 μm.

Table 4.2 shows the reservoir potentials estimated using the electrical resistor network analogy explained herein for the loading step and the injecting step. These values were used as a starting point for optimization of the electrokinetic injection. Reservoir potentials were slightly modified to adjust the amount of pinching during the loading step and the amount of pullback in the loading channels during the injection step. As can be seen, the voltages on reservoirs A and D are decreased in the loading step to create more pinching. The voltages on reservoirs B and F are reduced during the injection step to decrease the amount of pullback, so the consecutive loading step takes a shorter time, and the potentials on reservoir C and E are slightly decreased to prevent sample from dispersing into the gel loading channels. FIGS. 24A-24D show fluorescent images of the injection process. FIG. 24A shows the loading step in floating mode, when only a potential is applied to reservoir B and F, and the remaining reservoirs are at floating potential. As can be seen, the sample slightly diffuses horizontally. The amount of sample diffuses over time. FIG. 24B shows the loading step where the loaded sample is being 'pinched' by applying potentials in the other reservoirs, which counteracts the time dependent sample diffusion. FIGS. 24C and 24D show the injection step, where the loaded sample plug is being injected horizontally, while the sample in the loading channels is being pulled back, preventing it from leaking during the injection step.

Electrophoretic Mobility

FIG. 25A shows the electropherogram measured right before the beginning of the capture gel at a distance of 5.9 mm from the double-T injection for electric field strengths between 100 V/cm and 400 V/cm. The text indicates the time at which the maximum intensity was observed at the sensing point, which is thus the time it takes for a sample to reach the capture gel after the injection step is initiated. As expected, higher electric field strengths result in shorter transport times. At the highest electric field of 400 V/cm, the plug moves so fast that no well-defined peak profile can be distinguished. This can be attributed to the limited sample frequency of the photosensor of about 3 Hz. Furthermore, the curves at 200 and 400 V/cm show a decrease below 1 at the beginning of the measurement. This indicates that the previous sample was not completely washed out when the measurement started. However, this does not influence the location of the peaks. FIG. 25B shows the plug velocity versus the electric field strength, calculated from the observed peak times. These two parameters show a linear relationship ($R2=0.96$). The slope of this curve, and thus the electrophoretic mobility of the sample, is 7.79 cm2/V s. This mobility corresponds to values found in literature for BSA, ranging between 6.7, 8.0 and 8.7 cm2/V s, which thus confirms that the electrokinetic transport is occurring as expected.

Injected Mass

FIG. 26A shows an injected sample plug moving through the channel. Although this plug shows a parabolic profile, it does not disperse during the injection process but the shape of the plug stays constant. The measured fluorescence intensity profile over the length of the injected plug was converted to a concentration profile shown in FIG. 26B, using the calibration curve from FIG. 23. Summation of all concentrations multiplied by the volume associated with each data point according to equation 3.8 results in an injected mass of 0.4 ng per injection for a concentration of 0.2 p,M of BSA in the sample inlet.

Protein Capturing

FIG. 27A shows a fluorescent image of the capture gel after 0, 4, 7, 10 and 13 electrokinetic injections of fluorescent labeled BSA. The line indicates where the capture gel starts. Right of the line the channel is filled with the capture gel, while the channel to the left of the line is filled with regular polyacrylamide. As can be seen, the concentration of BSA in the capture gel increases after each injection, while no BSA is being captured by the regular polyacrylamide gel. This confirms that the antibody conjugation chemistry works and the resulting capture gel is capable of capturing BSA. The BSA is not saturating the capture gel downstream immediately upon capturing. FIG. 27B shows that BSA is being captured over the entire length of the capture gel and the intensity curve gradually increases almost uniformly over the width. However, the electrical resistor grid analogy assumes a gradual saturation of the capture gel downstream. Capture efficiency can be improved by reducing the electric field strength during electrophoresis, by increasing the concentration of antibodies in the capture gel, or by choosing an antibody-antigen pair with a lower dissociation constant $K_d$. Alternatively, instead of antibodies, oligonugleotides can be copolymerized in the capture gel to capture single stranded DNA, as the affinity between DNA strands is very high.

Impedance Spectroscopy

FIGS. 28A and 28B show the magnitude and phase of the impedance measured in the chip at five different concentrations of TG buffer using the four-electrode setup. The five measurement results have the same shape; a flat plateau at low frequency and a negative slope at high frequency. The flat plateau, combined with the zero degree phase angle at frequencies below 103 Hz represents the pure resistive behavior of the solution. This shows that the chip can distinguish solutions based on conductivity.

Integration—Bubble Formation on the Electrodes

Figure 29A:
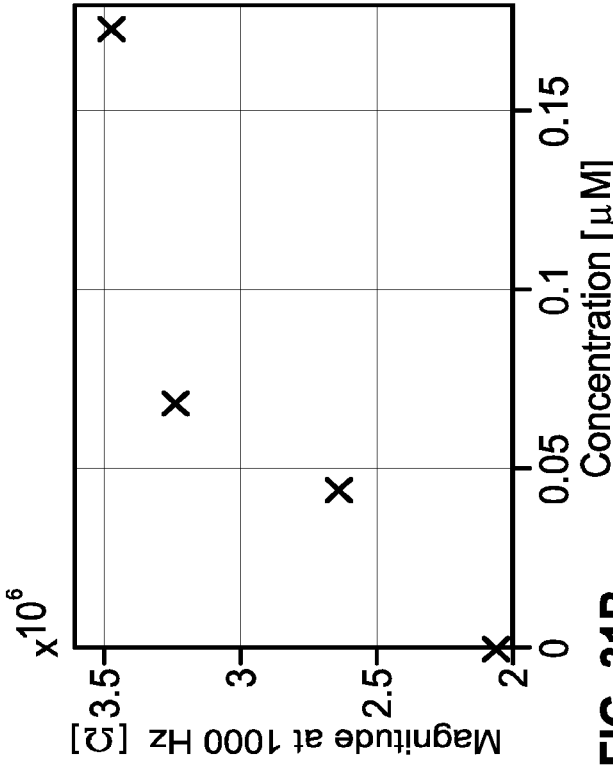
FIG. 29A is an illustration of the bipolarity of integrated electrodes and the resulting currents during electrophoresis.
Figure 29B:
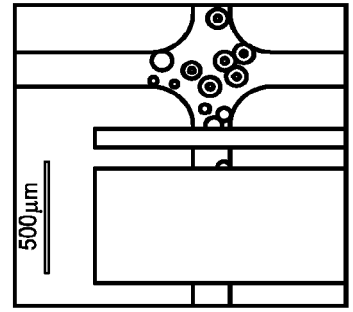
FIG. 29B is an illustration of bubble formation on electrodes at an electric field strength of 67V/cm.

Combining the electrokinetic injection, protein capturing and impedance measurements caused several integration issues. The main problem was bubble formation on the electrodes during electrophoresis. Even at low electric field strengths, down to 50 V/cm, bubbles started to nucleate at the edges of the electrodes, as can be seen in FIG. 29B. Once a bubble was present in the channel, the current during electrophoresis dropped and electrokinetic transport of the proteins stopped, which terminated the experiment. Furthermore, smaller bubbles forming on the electrode surface can cause a change in impedance and make the measurements unreliable as the increased impedance due to bubbles cannot be separated from the increase in impedance due to captured proteins.

During electrophoresis, an electric field is applied over the microchannel which can easily be in the order of hundreds of volts per centimeter. Contrarily, since the electrodes are excellent conductors, there is a negligible potential drop over the electrode. This is illustrated in FIG. 29A. This figures shows that one side of the electrode has a positive potential relative to the liquid, while the other side has a negative potential relative to the liquid. Consequently, one side acts as an anode while the other side acts as a cathode. When the potential drop over the electrode reaches above a certain threshold, either because the applied electric field is too high or the electrode is too wide, electrolysis of the water occurs on the edges of the electrodes which produces hydrogen and oxygen bubbles. This limit has been calculated by integrating the cathodic and anodic current, and using this result to estimate the potential difference over the electrode required to build up the charge necessary to generate steady bubble formation. The analysis shows that a voltage drop greater than 3 V over a 400 J-1 m wide electrode will result in bubble formation. This voltage drop corresponds to a critical electric field of about 75 V/em, which agrees with to the observations in this chip, and is significantly lower than some demonstrated analytical microfluidic electrophoretic microchips without integrated electrodes that use electric fields of 320 and 275 V/em, respectively. This lower electric field results in lower velocities of biomolecules and therefore slows down analysis.

Several approaches were considered to reduce the bubble formation, such as spin coating thin layers of COP dissolved in xylene over the electrodes to prevent direct contact between the electrodes and the gel. This configuration allows for conductivity measurements at high frequency if the capacitance of the thin layer is high enough. This method of impedance measurement is called contactless capacitive coupled conductivity measurement (C4D) and is well described in literature as a solution to solve bubble formation on electrodes in capillary electrophoresis. However, the capacity of the thinnest layer that could be spin coated, measured to be below 100 nm was too low to measure a distinctive difference between 0.1×, 1× and 10× TG buffers like in FIGS. 28A and 28B with the impedance analyzer setup, since it was limited to 12 V excitation voltage. Additional efforts to increase the capacitance of the thin film by incorporating silver nanowires in the COP film have reported an increase film capacitance by incorporating silver nanowires in nanocellulose paper, did not work since the nanowires did not dissolve in xylene. Therefore, it was decided to redesign the chip to shield the sensing electrodes from the electric field.

Impedance Change Upon Protein Capturing

Figure 30:
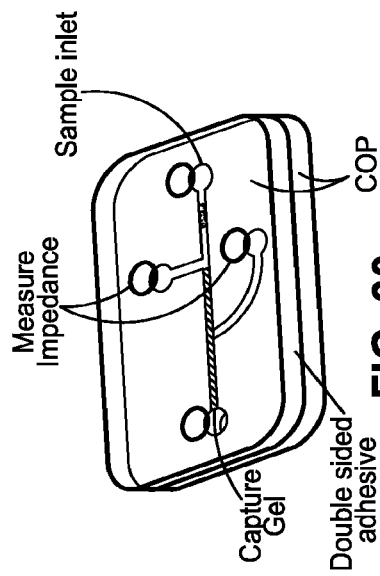
FIG. 30 illustrates a schematic design of a microfluidic chip including double sided adhesive and COP.

A more simplified proof of concept of the combination of protein capturing and impedance measurement was performed in a chip without integrated electrodes, where the impedance was measured between two reservoirs. Since the channels in the hot-embossed microchip are small (i.e. 200 µm×100 µm), the resistance between two reservoirs is above the measurable range of the impedance analyzer (107Ω@ 1 kHz). A microfluidic chip with larger channel dimensions of 1 mm×150 µm was fabricated out of double sided adhesive and used for these measurements, schematically shown in FIG. 30. The adhesive was laser cut to form the channels using a $CO_2$ laser and was laminated between two 1 mm sheets of COP. Before lamination, through holes were drilled in the top layer to create inlets using a drill press. The capture gel was positioned between the two sidechannels as shown in FIG. 30. Sample was injected from the sample inlet trough the capture gel, and washed out from the side channels. Impedance was measured in a two-electrode setup in the reservoirs of the sidechannels, using the same platinum electrodes as for electrophoresis.

Figure 31A:
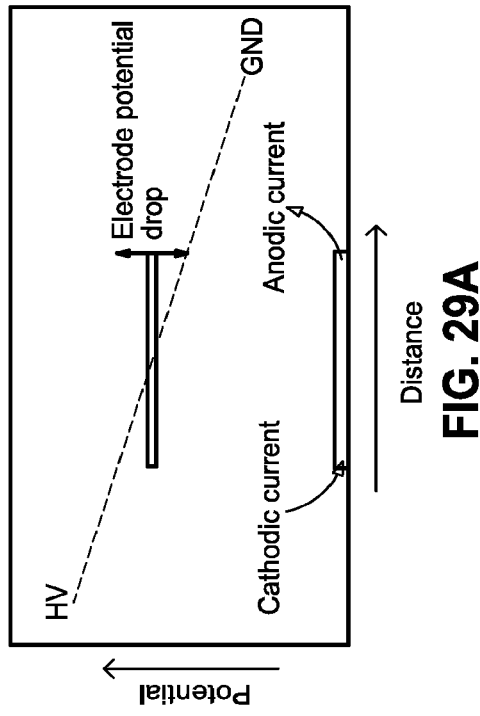
FIG. 31A illustrates a magnitude of the impedance after positioning the gels (0) and after 1, 2 and 3 injections of BSA, where the inset shows fluorescent microscopy images of the captured BSA after each injection.
Figure 31B:
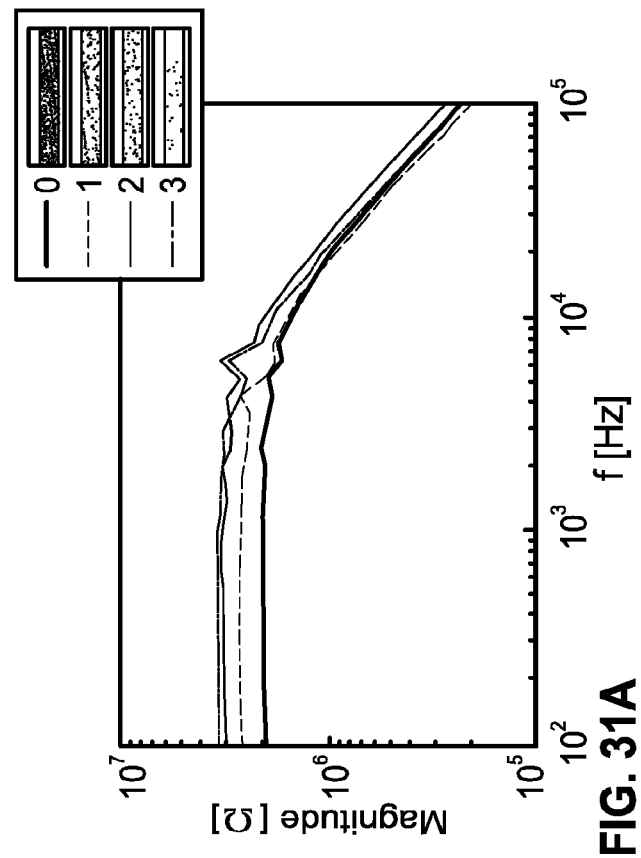
FIG. 31B illustrates the increase of impedance per injection at 1000 Hz, indicating an increase in impedance after each injection.

FIGS. 31A and 31B shows the change in impedance upon the capturing of BSA inside a microchannel in a simple chip made out of double sided adhesive between two flat pieces of COP. Because the channel has a larger cross-sectional area, the hydraulic resistance of the channel is smaller which made it more difficult to position the hydrogels. After removing the injection manifold, there was no longer a clear interface between the capture gel and the transport gel. Moreover, this chip did not include the same kind of well characterized electrokinetic injection as the hot embossed chips and thus not each injecting contained the same amount of BSA. Nevertheless, as can be seen in FIG. 31A, the low frequency plateau in the magnitude of the impedance increases after each injection, which suggests that the capturing of the proteins indeed causes an increase in electrical resistance. Because the electrodes are not in contact with the sample, the effect of electrode fouling can be neglected. On the other hand, the change in impedance could also be attributed to the depletion of the running buffers in the reservoirs. A control experiment would be needed to validate that the protein binding indeed causes this change in impedance.

Redesign

A suggested solution to prevent bubble formation is to position the electrodes just outside of the transport/capture channel, which shields the electrodes from the electric field and prevents the electrodes from direct contact with the analyte. Such an arrangement is sketched in FIG. 32.

Figure 33A:
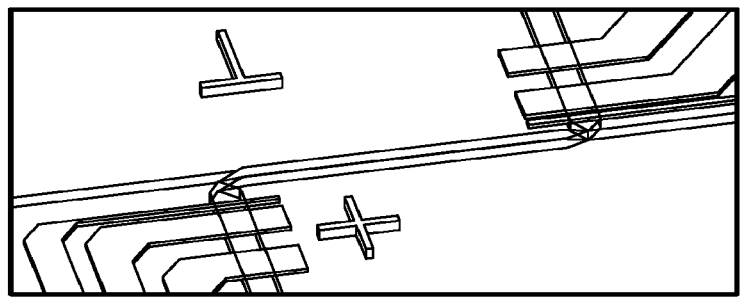
FIG. 33A illustrates a capture area of a chip.
Figure 33B:
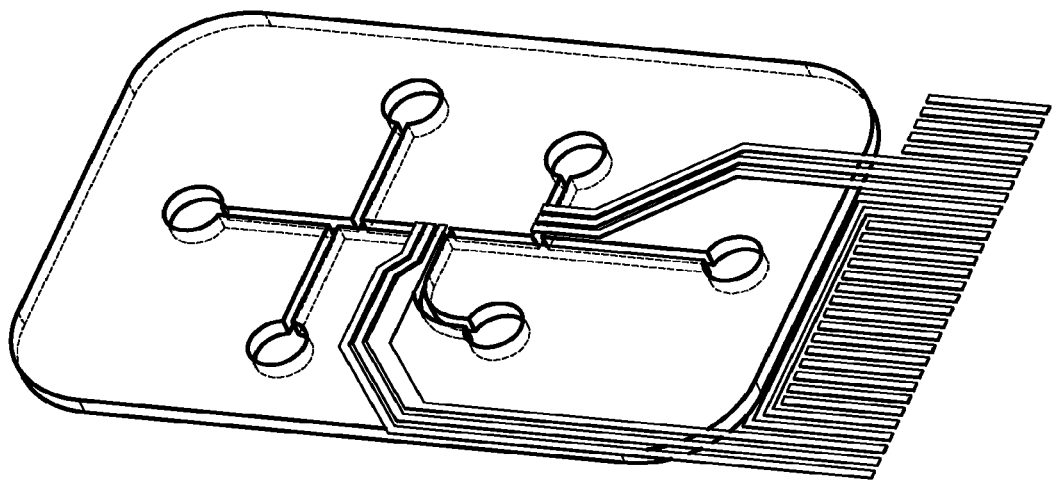
FIG. 33B illustrates a bonded chip.

The chip was redesigned to exclude the electrodes from the electric field during electrophoresis. A close up of the capture region is shown in FIG. 33A. The electrodes are positioned in sidechannels and a contraction is positioned between the sidechannels and the capture area to shield the electrodes from the electric field during electrophoresis. This design has the additional benefit that the sample, that will not enter the sidechannels during electrophoresis, will not directly touch the electrodes and thus prevents fouling of the electrodes during an experiment. A new aluminum mold was fabricated based on this design, COP chips were hot embossed and matching electrodes were fabricated and bonded into a chip as shown in FIG. 33B. However, although the material of the electrodes should be the same as all previous fabricated electrodes, they turned out not to bond well with the microfluidics using the previously established bonding procedures optimized for bonding COP. On every occasion, the electrode layer delaminated while injecting the hydrogel rendering the chip useless. A simple microfluidic layer with a main channel and two side channels for the electrodes was fabricated out of double sided adhesive to study how this redesign affected the maximum electric field over the chip. This redesigned allowed for electric fields over 300 V/cm, at the critical applied voltage, without the formation of bubbles on the electrodes, an increase in electric field strength of 6 times compared to the previous design. Table 4.3 show the maximum electric field for the old design, the new design and the approach where the electrodes were coated with COP. It shows that this redesign outperforms all other chins in maximum allowable electric field.

TABLE 4.3

Critical electric field before bubbles started to nucleate

|  | No coating | 0.05 mg/ml | 0.5 mg/ml | Redesign |
| --- | --- | --- | --- | --- |
| $E_{max}$ [V/cm] | 50 | 83.3 | 100 | 300+ |

In this work, a microfluidic device with integrated electrodes was designed and developed with the aim to test the hypothesis that capturing biomolecules in a 3D matrix can decouple the sensitivity and dynamic range of an impedance immunosensor. This development covered a wide range of topics, including chip fabrication, hydrogel chemistry, electrokinetically driven microfluidics, impedance spectroscopy and fluorescent microscopy. The device was designed to be fabricated out of thermoplastics for good manufacturability and scalability. Large quantities of microfluidic chips could easily be fabricated using a single aluminum mold. Electrodes and microfluidics were successfully bonded using solvent assisted thermal bonding. The chip was designed to utilize electrokinetic injection to dispense small, quantified volumes of sample into the microfluidic detection channel. Reservoir potentials and corresponding currents calculated using an electronic circuit analogy showed to give a good estimation for the injection of charged proteins trough the microchannels. The injection was successfully demonstrated and characterized and was proven to be a robust way to control small sample volumes.

Antibodies were successfully copolymerized in a linear polyacrylamide hydrogel after incubating N-hydroxysuccinimide acrylate. This was shown to be an effective, low-cost method to create a 3D matrix with antibodies that added minimal mass. A novel method was demonstrated to inject linear polymerized hydrogels into the chip and carefully position the capture gel between the electrodes under the microscope, using two syringes and a custom designed injection manifold. This method allows to polymerize hydrogels outside of the chip in large batches and fill the chips with gels prior to use. Removing the injection manifold from the chip, however, caused a slight displacement of the interface between the two gels. This is not a problem for a proof of principle device that aims at characterizing the relationship between sensitivity and dynamic range, but would certainly need to be addressed in order to further develop this concept towards a robust functional sensor. Preferably, a new multifunctional manifold should be developed that can inject gels, provide reservoirs and includes the electrodes for electrophoresis at the same time. The electrokinetic injection and protein capturing in a hydrogel were jointly demonstrated inside a microfluidic chip, by capturing fluorescent labeled BSA. After each injection, a steady increase in fluorescent signal was observed thus indicating that the capture gels indeed are able to capture BSA. However, The BSA did not bind to the capture gel upon contact as assumed in the model, but dispersed over a wide range of the capture gel. In order to demonstrate decoupling, a higher concentration of antibodies or acrylamide should be used in the capture gel to improve the binding efficiency. Alternatively, the electric field during electrophoresis could be reduced or an antibody-antigen pair should be chosen with a higher affinity, and thus a lower dissociation rate. Alternatively, single strands of DNA could be used instead of proteins because of its high affinity.

The integrated electrodes were demonstrated to be able to distinguish different concentrations of buffer solutions inside the chip, thus proving the capability as a microfluidic conductivity sensor. Integrating the electrodes was problematic as bubbles started to form on the electrodes during electrophoresis. The observations of bubble formation matched with the theory on bipolar electrodes described in the literature, and a redesign was proposed that in preliminary results indeed reduced the problem with bubble formation. Unfortunately, the redesigned electrodes did not bond with the new microfluidics even though all processes were identical. A new batch of electrodes should be fabricated and bonded with the microfluidics to perform the final experiments needed to fully test the hypothesis. Regardless of the fabrication issues, a simplified chip was manufactured using double sided adhesive tape, and demonstrated an increase in impedance upon protein binding.

The result of this work is the development of a robust microfluidic platform that is capable of electrokinetic sample handling, dispensing well-defined small volumes, specific protein capturing in a 3D matrix and impedance measurements, and the design and setup of instrumentation to operate this platform. Apart from testing the hypothesis of decoupling, further work could also look into developing this microfluidic platform into a real diagnostics application, by multiplexing the assay and incorporating positive and negative controls and calibration standards. The assay has to be tested for non-specific binding and cross-reactivity and the response of the sensor should be characterized in order to investigate how the sensitivity and dynamic range compare to established assays. Further research should also look into miniaturizing the instrumentation to create an integrated reader for the chip to create a true benchtop immunosensor.

Alternative Implementations

According to some implementations of the present disclosure, instead of using a monomer with a reactive group such as NSA to introduce a monomer group to the probe, biotinylated probe can be used that can be coupled with copolymerized streptavidin.

According to some implementations of the present disclosure, DNA or other sequence-specific binding can be used to functionalize the gel. Either for nucleic acid detection or for nucleic acid-labeled proteins and other transducer/capture moieties.

According to some implementations of the present disclosure, instead of using a monomer with a reactive group one can use oligomers with reactive groups.

According to some implementations of the present disclosure, instead of copolymerizing monomer modified probes, one can copolymerize reactive groups in the polymers that bind with the probes after polymerization.

According to some implementations of the present disclosure, a small amount of cross linker can be added to the linear polymerized gel such that it is less likely to migrate inside the device and smaller pore size can be achieved.

According to some implementations of the present disclosure, instead of preparing the gel outside of the sensor and inserting it afterwards, one can polymerize the gel directly inside the device using UV polymerization.

According to some implementations of the present disclosure, instead of using polyacrylamide gel as a hydrogel matrix, one can also use polymethacrylamide, PEG, PEGDA, PDMS, Agarose, any other sieving matrix, etc. or any combination thereof.

According to some implementations of the present disclosure, instead of using electrophoresis, one can also use a pressure driven flow, diffusion, capillary action, electroosmosis, acoustophoresis, electromagnetism, an evaporative driven pump, or a thermally driven flow.

According to some implementations of the present disclosure, instead of using a hydrogel, one immobilize probes on the surface of beads, a sol gel, 3D structures inside the channel such as posts or on the walls of capillaries, nanochannels, or pores.

According to some implementations of the present disclosure, instead of capturing targets inside a solution, the sensor can also be used for gas measurements as gas containing targets can be flown through the 3D matrix.

According to some implementations of the present disclosure, instead of capturing protein, the 3D matrix can also be used to capture small molecules, DNA, RNA, cells, viruses, nanoparticles, particulates or organisms.

According to some implementations of the present disclosure, instead of using antibodies, the 3D matrix can also be functionalized with single or double stranded DNA, single or double stranded RNA, cells, oligonucleotides, aptamers, ligands, lipids, peptides, etc.

According to some implementations of the present disclosure, instead of capturing only specific targets using a target and probe with a high affinity, the sensor can also be used to capture non-specific targets based on size by modifying the pore size of the 3D matrix or based charge by electrical forces by applying a potential to the 3D matrix or based on magnetic force by either using magnetic particles as targets or by magnetizing the 3D matrix, by which it can capture particles based on magnetic susceptibility.

According to some implementations of the present disclosure, instead of using a four electrode setup, one can also use a two or three electrode setup or an array of multiple electrodes.

According to some implementations of the present disclosure, instead of using electrical impedance to sense the measuring mechanisms, one can also use acoustical impedance, thermal impedance, or electromagnetic/optical wave impedance as a detection mechanism.

According to some implementations of the present disclosure, a labeling step can be used after the binding step to increase the signal output. This can be done by using any probe described herein.

According to some implementations of the present disclosure, additionally, as a labeling step, any probe described herein can be conjugated with nanoparticles, small molecules (e.g. fluorophores, metallocene), beads, DNA or proteins to further increase the output signal.

According to some implementations of the present disclosure, instead of hot embossing the channel (e.g., a microfluidic layer), it can also be injection molded, vacuum formed, thermoformed, blow molded, milled, drilled, casted, etched, 3D printed, laser cut, waterjet cut or engraved.

According to some implementations of the present disclosure, the fluidics part (e.g., the microfluidic layer) of the chip can be fabricated out of polymers, natural materials, such as cellulose, chitosan, wood, stone, etc., glasses, ceramics, metals, silicon, tissue, or any combination thereof.

According to some implementations of the present disclosure, instead of using planar electrodes, the electrodes can be placed concentric around the channel or on either side of the channel, or be composed of porous material (e.g., metal frits).

According to some implementations of the present disclosure, sensors can be designed to quantify properties other than biomolecule concentrations, such as mass, capacitance, pressure, flow rate, etc. This approach is versatile in application. In some implementations, these sensors exhibit some degree of saturation at the input side to allow decoupling of the sensitivity and dynamic range.

Figure 32:
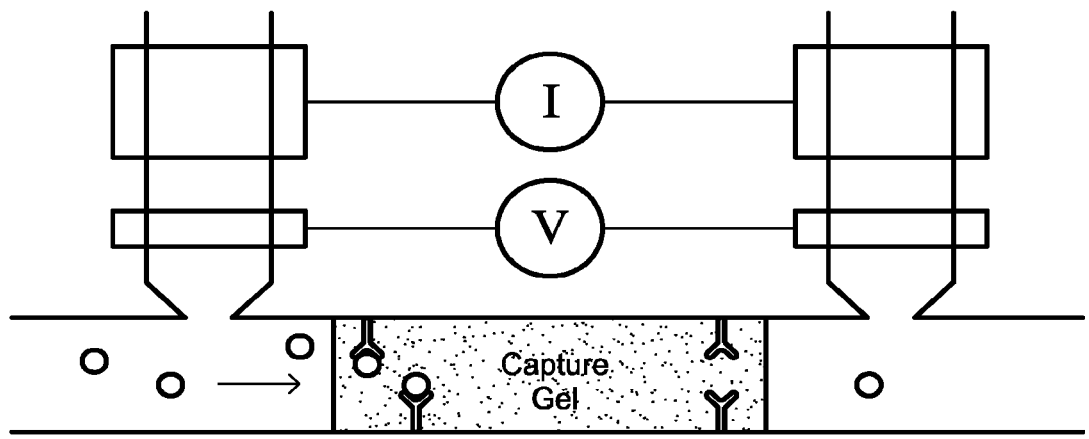
FIG. 32 illustrates a sensing area of a chip with impedance measurement electrodes separated from a main capture channel.

According to some implementations of the present disclosure, as shown in FIG. 32, electrodes can be placed in side-channels (e.g., electrode channels) perpendicular to the main channel including the capture gel therein to reduce the potential drop over the electrodes during electrophoresis. According to some such implementations of the present disclosure, a small contraction can be positioned at the entrance of this side-channel to further reduce the potential drop over the electrodes during electrophoresis.

The channels described in the present disclosure (e.g., the main channel, the sample channels, the electrode channels, etc.) can have any cross-sectional shape (e.g., circular, square, rectangular, oval, curved, triangular, polygonal, trapezoidal, etc., or any combination thereof) and any size (e.g., a cross-sectional area between about 0.5 square nanometers and about 200 square millimeters, a cross-sectional area between about 0.5 square nanometers and about 80 square nanometers, a cross-sectional area between about 300 square nanometers and about 200 square millimeters, a cross-sectional area of about 0.01 square millimeters, etc.).

In some implementations, a cross-sectional area of the main channel and/or of the capture material therein is larger than a size (e.g., maximum diameter, maximum height, maximum width, maximum cross-sectional area, etc.) of a target. In some such implementations, the cross-sectional area of the main channel and/or of the capture material therein is at least about two times, five times, ten times, twenty times, fifty times, one hundred time, one thousand times, etc. larger than a maximum cross-sectional area of the target.

What is claimed is:

1. A fluidic device comprising:
   a fluidic layer including a main channel, a pair of sample channels fluidly coupled to the main channel, and two or more electrode channels fluidly coupled to the main channel, the pair of sample channels being configured to receive and introduce a sample material into the device, the sample material including an analyte;
   a capture material positioned in a portion of the main channel that is spaced from the pair of sample channels, the capture material having a three-dimensional matrix of receptors therein configured to bond with the analyte; and
   an electronics layer including electrodes positioned at least partially within the two or more electrode channels such that the electrodes are configured to measure an electrical resistance through a portion of the capture material.

2. The fluidic device of claim 1, wherein the two or more electrodes are positioned in the pair of sample channels.

3. The fluidic device of claim 1, wherein a first of the pair of sample channels extends from a first side of the main channel and a second of the pair of sample channels extends from a second opposing side of the main channel.

4. The fluidic device of claim 3, wherein the first sample channel is linearly offset from the second sample channel along a length of the main channel.

5. The fluidic device of claim 4, wherein the linear offset of the pair of sample channels defines a sample portion of the main channel.

6. The fluidic device of claim 1, wherein the electrodes include an inner pair of electrodes and an outer pair of electrodes, the inner pair of electrodes being configured to measure the electrical resistance through the portion of the capture material responsive to a current being applied to the outer pair of electrodes.

7. The fluidic device of claim 1, wherein the electronics layer is directly bonded to the fluidic layer.

8. The fluidic device of claim 1, wherein the electronics layer is coupled to the fluidic layer such that each of the electrodes is spaced from all receptors bonded with the analyte during the measuring of the electrical resistance.

9. The fluidic device of claim 1, wherein the fluidic layer further includes two or more electrode channels fluidly coupled to the main channel and extending therefrom.

10. The fluidic device of claim 9, wherein the electronics layer is coupled to the fluidic layer such that a first of the electrodes is in fluid communication with the main channel via a first of the two or more electrode channels and a second of the electrodes is in fluid communication with the main channel via a second of the two or more electrode channels.

11. The fluidic device of claim 10, wherein the first electrode channel is coupled to the main channel via a first contraction and the second electrode channel is coupled to the main channel via a second contraction.

12. The fluidic device of claim 1, wherein the fluidic device is a microfluidic device.

13. The fluidic device of claim 1, wherein the three-dimensional matrix of receptors is evenly distributed throughout a volume of the capture material.

14. The fluidic device of claim 1, wherein a length and a cross-sectional area of the capture material is defined by the main channel.

15. The fluidic device of claim 1, wherein the main channel has a width of about 50 micrometers and a height of about 50 micrometers or about 100 micrometers.

16. The fluidic device of claim 1, wherein the main channel has a width of about 100 micrometers and a height of about 50 micrometers or about 100 micrometers.

17. The fluidic device of claim 1, wherein the main channel extends between and is fluidly coupled with a first reservoir and a second reservoir.

18. The fluidic device of claim 17, wherein the first sample channel extends between and is fluidly coupled with a third reservoir and the main channel, and the second sample channel extends between and is fluidly coupled with a fourth reservoir and the main channel.

19. The fluidic device of claim 18, wherein responsive to a potential being applied across the third reservoir and the fourth reservoir, the sample material is configured to move from the third reservoir towards the fourth reservoir such that a portion of the sample material is positioned in the main channel.

20. The fluidic device of claim 19, wherein responsive to a potential being applied across the first reservoir and the second reservoir, the portion of the sample material in the main channel is configured to move along the main channel towards the second reservoir such that at least some of the analyte in the portion of the sample material bonds with the three-dimensional matrix of receptors in the capture material.

21. The fluidic device of claim 1, wherein the capture material is a hydrogel.

22. The fluidic device of claim 21, wherein the hydrogel includes polyacrylamide.

23. The fluidic device of claim 1, wherein the receptors include antibodies, single-stranded DNA, nucleic acids, one or more proteins, or any combination thereof.

24. The fluidic device of claim 23, wherein the one or more proteins include one or more transcription factors, one or more lectins, one or more antibodies, one or more short peptides, or any combination thereof.

25. The fluidic device of claim 1, wherein the receptors include one or more lipids, one or more cells, bacteria, one or more viruses, or any combination thereof.

26. The fluidic device of claim 1, wherein the receptors include one or more small chemical molecules, one or more carbohydrates, one or more glycosylated molecules, or any combination thereof.

27. The fluidic device of claim 1, wherein the fluidic device is a nanofluidic device.

28. The fluidic device of claim 1, wherein the fluidic device is a macrofluidic device.

29. The fluidic device of claim 1, the capture material having a length that is associated with a dynamic range of the fluidic device and a cross-sectional area that is associated with a sensitivity of the fluidic device.

30. The fluidic device of claim 29, wherein the sensitivity of the fluidic device increases with a reduction of the cross-sectional area of the capture material, and the sensitivity of the fluidic device decreases with an increase of the cross-sectional area of the capture material.

31. The fluidic device of claim 29, wherein the dynamic range of the fluidic device increases with an increase of the length of the capture material, and the dynamic range of the fluidic device decreases with a decrease of the length of the capture material.

32. The fluidic device of claim 29, wherein the cross-sectional area of the capture material is selected based at least in part on a size of the analyte.

33. The fluidic device of claim 29, wherein the cross-sectional area of the capture material is between about 0.5 square nanometers and about 80 square nanometers.

34. The fluidic device of claim 29, wherein the cross-sectional area of the capture material is between about 300 square nanometers and about 200 square micrometers.

35. The fluidic device of claim 29, wherein the cross-sectional area of the capture material is between about 0.5 square micrometer and about 200 square millimeters.

36. The fluidic device of claim 1, wherein the electronics layer comprises a printed circuit board (PCB).

* * * * *